(12) United States Patent
Pflueger et al.

(10) Patent No.: US 8,578,938 B2
(45) Date of Patent: Nov. 12, 2013

(54) APPARATUS AND METHODS FOR TREATING SLEEP APNEA

(75) Inventors: D. Russell Pflueger, San Juan Capistrano, CA (US); Christopher Paul Thompson, Austin, TX (US)

(73) Assignee: Quiescence Medical, Inc., Dana Point, CA (US)

( * ) Notice: Subject to any disclaimer, the term of this patent is extended or adjusted under 35 U.S.C. 154(b) by 834 days.

(21) Appl. No.: 12/557,386

(22) Filed: Sep. 10, 2009

(65) Prior Publication Data
US 2010/0000550 A1 Jan. 7, 2010

Related U.S. Application Data

(63) Continuation of application No. 10/541,255, filed on Mar. 27, 2006, now Pat. No. 8,104,478, which is a continuation-in-part of application No. 10/624,915, filed on Jul. 22, 2003, now Pat. No. 7,992,566.

(60) Provisional application No. 60/436,945, filed on Dec. 30, 2002, provisional application No. 60/437,058, filed on Dec. 30, 2002.

(51) Int. Cl.
*A61M 16/00* (2006.01)
(52) U.S. Cl.
USPC .......... 128/848; 128/200.24; 128/200.26; 128/207.14; 128/859; 128/860; 606/108; 606/196
(58) Field of Classification Search
USPC .......... 128/848, 200.26, 200.24, 207.14, 859, 128/860, 861, 862, 863
See application file for complete search history.

(56) References Cited

U.S. PATENT DOCUMENTS

| | | | |
|---|---|---|---|
| 2,574,623 | A | 11/1951 | Clyde |
| 4,580,568 | A | 4/1986 | Gianturco |
| 4,665,918 | A | 5/1987 | Garza et al. |
| 4,732,152 | A | 3/1988 | Wallsten et al. |
| 4,794,924 | A | 1/1989 | Eliachar |
| 4,821,715 | A | 4/1989 | Downing |
| 4,830,008 | A | 5/1989 | Meer |
| 4,848,343 | A | 7/1989 | Wallsten et al. |

(Continued)

FOREIGN PATENT DOCUMENTS

| DE | 19920114 A1 * | 11/2000 |
|---|---|---|
| DE | 458679 | 6/2002 |

(Continued)

OTHER PUBLICATIONS

Machine translation provided by the European Patent Office, Fege (DE19920114A1), Nov. 9, 2000, Description of DE19920114, pp. 1-3.*

(Continued)

*Primary Examiner* — Clinton T Ostrup

(57) ABSTRACT

An apparatus and method for treating sleep apnea and/or snoring is provided. The apparatus includes an appliance sized and structured to be placed in the pharyngeal region of a human or animal and being effective in treating sleep apnea and/or snoring, for example in maintaining openness of an oropharyngeal region of a human or animal during natural sleep, advantageously while not interfering with normal functioning of the epiglottis. The appliance may be made of a super elastic material, for example, Nitinol, and may be submucosally implanted in the pharyngeal walls.

9 Claims, 15 Drawing Sheets

(56) References Cited

U.S. PATENT DOCUMENTS

| | | | |
|---|---|---|---|
| 4,875,480 A | 10/1989 | Imbert | |
| 4,950,227 A | 8/1990 | Savin et al. | |
| 4,978,323 A * | 12/1990 | Freedman | 600/12 |
| 5,007,926 A | 4/1991 | Derbyshire | |
| 5,026,377 A | 6/1991 | Burton et al. | |
| 5,037,427 A | 8/1991 | Herada et al. | |
| 5,046,512 A | 9/1991 | Murchie | |
| 5,048,518 A | 9/1991 | Eliachar et al. | |
| 5,052,409 A | 10/1991 | Tepper | |
| 5,059,211 A | 10/1991 | Stack et al. | |
| 5,061,275 A | 10/1991 | Wallsten et al. | |
| 5,064,435 A | 11/1991 | Porter | |
| 5,065,756 A | 11/1991 | Rapoport | |
| 5,071,407 A | 12/1991 | Termin et al. | |
| 5,078,720 A | 1/1992 | Burton et al. | |
| 5,117,816 A | 6/1992 | Shapiro | |
| 5,133,354 A | 7/1992 | Kallok | |
| 5,147,370 A | 9/1992 | McNamara et al. | |
| 5,176,618 A | 1/1993 | Freedman | |
| 5,178,156 A | 1/1993 | Takishima et al. | |
| 5,190,053 A | 3/1993 | Meer | |
| 5,201,757 A | 4/1993 | Heyn et al. | |
| 5,204,382 A | 4/1993 | Wallace et al. | |
| 5,258,028 A | 11/1993 | Ersek et al. | |
| 5,281,219 A | 1/1994 | Kallok | |
| 5,284,161 A | 2/1994 | Karell | |
| 5,290,289 A | 3/1994 | Sanders et al. | |
| 5,292,331 A | 3/1994 | Boneau | |
| 5,306,294 A | 4/1994 | Winston et al. | |
| 5,355,874 A | 10/1994 | Bertram | |
| 5,360,401 A | 11/1994 | Turnland | |
| 5,372,600 A | 12/1994 | Beyar et al. | |
| 5,383,926 A | 1/1995 | Lock et al. | |
| 5,441,515 A | 8/1995 | Khosravi et al. | |
| 5,451,406 A | 9/1995 | Lawin et al. | |
| 5,456,662 A | 10/1995 | Edwards et al. | |
| 5,474,563 A | 12/1995 | Myler et al. | |
| 5,476,505 A | 12/1995 | Limon | |
| 5,494,029 A | 2/1996 | Lane et al. | |
| 5,514,131 A | 5/1996 | Edwards et al. | |
| 5,534,007 A | 7/1996 | St. Germain et al. | |
| 5,540,733 A | 7/1996 | Testerman et al. | |
| 5,571,135 A | 11/1996 | Fraser et al. | |
| 5,582,184 A | 12/1996 | Erickson et al. | |
| 5,591,216 A | 1/1997 | Testerman et al. | |
| 5,603,698 A | 2/1997 | Roberts et al. | |
| 5,611,355 A | 3/1997 | Hilsen | |
| 5,618,299 A | 4/1997 | Khosravi et al. | |
| 5,632,771 A | 5/1997 | Boatman et al. | |
| 5,642,737 A | 7/1997 | Parks | |
| 5,643,309 A | 7/1997 | Myler et al. | |
| 5,649,540 A | 7/1997 | Alvarez et al. | |
| 5,664,567 A | 9/1997 | Linder | |
| 5,669,377 A | 9/1997 | Fenn | |
| 5,674,191 A | 10/1997 | Edwards et al. | |
| 5,682,903 A | 11/1997 | Meade | |
| 5,683,451 A | 11/1997 | Lenker et al. | |
| 5,709,703 A | 1/1998 | Lukic et al. | |
| 5,718,224 A | 2/1998 | Muchin | |
| 5,718,702 A | 2/1998 | Edwards | |
| 5,720,275 A | 2/1998 | Patil et al. | |
| 5,738,114 A | 4/1998 | Edwards | |
| 5,772,668 A | 6/1998 | Summers et al. | |
| 5,776,142 A | 7/1998 | Gunderson | |
| 5,791,341 A | 8/1998 | Bullard | |
| 5,792,067 A | 8/1998 | Karell | |
| 5,792,478 A | 8/1998 | Lawin et al. | |
| 5,797,952 A | 8/1998 | Klein | |
| 5,800,379 A | 9/1998 | Edwards | |
| 5,815,904 A | 10/1998 | Clubb et al. | |
| 5,836,966 A | 11/1998 | St. Germain | |
| 5,843,021 A | 12/1998 | Edwards et al. | |
| 5,868,138 A | 2/1999 | Halstrom | |
| RE36,120 E | 3/1999 | Karell | |
| 5,893,365 A | 4/1999 | Anderson | |
| 5,897,579 A | 4/1999 | Sanders | |
| 5,911,752 A | 6/1999 | Dustrude et al. | |
| 5,922,006 A | 7/1999 | Sugerman | |
| 5,950,624 A | 9/1999 | Hart | |
| 5,954,050 A | 9/1999 | Christopher | |
| 5,970,975 A | 10/1999 | Estes et al. | |
| 5,979,456 A | 11/1999 | Magovern | |
| 5,980,533 A | 11/1999 | Holman | |
| 5,983,136 A | 11/1999 | Kamen | |
| 5,988,170 A | 11/1999 | Thomas | |
| 6,004,342 A | 12/1999 | Filis | |
| 6,019,779 A | 2/2000 | Thorud et al. | |
| 6,022,343 A | 2/2000 | Johnson et al. | |
| 6,027,516 A | 2/2000 | Kolobow et al. | |
| 6,027,863 A | 2/2000 | Donadio, III | |
| 6,033,394 A | 3/2000 | Vidlund et al. | |
| 6,058,931 A | 5/2000 | Muchin | |
| 6,090,115 A | 7/2000 | Beyar et al. | |
| 6,092,523 A | 7/2000 | Belfer | |
| 6,098,616 A | 8/2000 | Lundy, Jr. et al. | |
| 6,106,541 A | 8/2000 | Hurbis | |
| 6,110,164 A | 8/2000 | Vidlund | |
| 6,123,082 A | 9/2000 | Berthon-Jones | |
| 6,126,611 A | 10/2000 | Bourgeois et al. | |
| 6,126,657 A | 10/2000 | Edwards | |
| 6,129,084 A | 10/2000 | Bergerson | |
| 6,132,460 A | 10/2000 | Thompson | |
| 6,132,461 A | 10/2000 | Thompson | |
| 6,161,541 A | 12/2000 | Woodson | |
| 6,161,542 A | 12/2000 | Halstrom | |
| 6,171,314 B1 | 1/2001 | Rotramel | |
| 6,183,493 B1 | 2/2001 | Zammit | |
| 6,238,411 B1 | 5/2001 | Thorner | |
| 6,238,430 B1 | 5/2001 | Klumb et al. | |
| 6,240,316 B1 | 5/2001 | Richmond et al. | |
| 6,248,122 B1 | 6/2001 | Klumb et al. | |
| 6,250,307 B1 | 6/2001 | Conrad et al. | |
| 6,254,631 B1 | 7/2001 | Thompson | |
| 6,257,236 B1 | 7/2001 | Dutkiewicz | |
| 6,270,512 B1 | 8/2001 | Rittmann | |
| 6,273,876 B1 | 8/2001 | Klima et al. | |
| 6,305,376 B1 | 10/2001 | Thornton | |
| 6,306,141 B1 | 10/2001 | Jervis | |
| 6,312,463 B1 | 11/2001 | Rourke et al. | |
| 6,325,064 B1 | 12/2001 | Thornton | |
| 6,328,753 B1 * | 12/2001 | Zammit | 606/196 |
| 6,329,352 B1 | 12/2001 | Meyer et al. | |
| 6,345,202 B2 | 2/2002 | Richmond et al. | |
| 6,358,274 B1 | 3/2002 | Thompson | |
| 6,363,935 B1 | 4/2002 | Boussignac | |
| 6,371,112 B1 | 4/2002 | Bibi | |
| 6,371,953 B1 | 4/2002 | Beyar et al. | |
| 6,371,979 B1 | 4/2002 | Beyar et al. | |
| 6,374,824 B1 | 4/2002 | Thornton | |
| 6,379,311 B1 | 4/2002 | Gaumond et al. | |
| 6,386,199 B1 | 5/2002 | Alfery | |
| 6,390,096 B1 | 5/2002 | Conrad et al. | |
| 6,401,717 B1 | 6/2002 | Conrad et al. | |
| 6,406,490 B1 | 6/2002 | Roth | |
| 6,408,852 B2 | 6/2002 | Tielemans | |
| 6,415,796 B1 | 7/2002 | Conrad et al. | |
| 6,419,641 B1 | 7/2002 | Mark et al. | |
| 6,427,686 B2 | 8/2002 | Augustine et al. | |
| 6,431,174 B1 | 8/2002 | Knudson et al. | |
| 6,432,128 B1 | 8/2002 | Wallace et al. | |
| 6,439,238 B1 | 8/2002 | Brenzel et al. | |
| 6,447,522 B2 | 9/2002 | Gambale et al. | |
| 6,450,169 B1 | 9/2002 | Conrad et al. | |
| 6,453,905 B1 | 9/2002 | Conrad et al. | |
| 6,474,339 B1 | 11/2002 | Grosbois et al. | |
| 6,475,232 B1 | 11/2002 | Babbs et al. | |
| 6,485,524 B2 | 11/2002 | Strecker | |
| 6,488,700 B2 | 12/2002 | Klumb et al. | |
| 6,502,574 B2 | 1/2003 | Stevens et al. | |
| 6,513,530 B2 | 2/2003 | Knudson et al. | |
| 6,513,531 B2 | 2/2003 | Knudson et al. | |
| 6,516,806 B2 | 2/2003 | Knudson et al. | |
| 6,523,541 B2 | 2/2003 | Knudson et al. | |
| 6,523,542 B2 | 2/2003 | Knudson et al. | |

(56) References Cited

U.S. PATENT DOCUMENTS

| | | |
|---|---|---|
| 6,523,543 B2 | 2/2003 | Conrad et al. |
| 6,546,936 B2 | 4/2003 | Knudson et al. |
| 6,578,580 B2 | 6/2003 | Conrad et al. |
| 6,601,584 B2 | 8/2003 | Knudson et al. |
| 6,601,585 B1 | 8/2003 | Conrad et al. |
| 6,626,181 B2 | 9/2003 | Knudson et al. |
| 6,634,362 B2 | 10/2003 | Conrad et al. |
| 6,636,767 B1 | 10/2003 | Knudson et al. |
| 6,742,524 B2 | 6/2004 | Knudson et al. |
| 6,793,672 B2 | 9/2004 | Khosravi et al. |
| 6,955,172 B2 | 10/2005 | Nelson et al. |
| 7,363,926 B2 | 4/2008 | Pflueger et al. |
| 7,381,222 B2 | 6/2008 | Pflueger et al. |
| 7,647,931 B2 | 1/2010 | Pflueger et al. |
| 7,992,566 B2 | 8/2011 | Pflueger et al. |
| 2001/0010010 A1 * | 7/2001 | Richmond et al. ............. 607/42 |
| 2001/0025642 A1 * | 10/2001 | Conrad et al. ................. 128/848 |
| 2001/0044587 A1 * | 11/2001 | Conrad et al. ................. 600/529 |
| 2001/0052344 A1 | 12/2001 | Doshi |
| 2002/0035994 A1 | 3/2002 | Stevens et al. |
| 2002/0040712 A1 | 4/2002 | Chou |
| 2002/0056462 A1 | 5/2002 | Conrad et al. |
| 2002/0108618 A1 | 8/2002 | Conrad et al. |
| 2002/0189727 A1 | 12/2002 | Peterson |
| 2003/0149445 A1 * | 8/2003 | Knudson et al. ............. 606/196 |
| 2003/0149488 A1 * | 8/2003 | Metzger et al. ............ 623/23.64 |
| 2004/0010308 A1 | 1/2004 | Zafrir-Pachter et al. |
| 2004/0020492 A1 | 2/2004 | Dubrul et al. |
| 2004/0045555 A1 | 3/2004 | Nelson et al. |
| 2004/0045556 A1 | 3/2004 | Nelson et al. |
| 2004/0049102 A1 | 3/2004 | Nelson et al. |
| 2004/0139975 A1 | 7/2004 | Nelson et al. |
| 2004/0172054 A1 | 9/2004 | Metzger et al. |
| 2004/0199045 A1 | 10/2004 | Knudson et al. |
| 2006/0235264 A1 | 10/2006 | Vassallo |
| 2007/0193587 A1 | 8/2007 | Boucher et al. |

FOREIGN PATENT DOCUMENTS

| | | |
|---|---|---|
| EP | 0292936 A2 | 11/1988 |
| EP | 0706808 A1 | 4/1996 |
| SU | 1553140 A1 | 3/1990 |
| WO | 9932057 A1 | 7/1999 |
| WO | WO 9932057 A1 * | 7/1999 |
| WO | 0059398 | 10/2000 |
| WO | 0119301 | 3/2001 |
| WO | 0123039 | 4/2001 |

OTHER PUBLICATIONS

Machine translation provided by the European Patent Office, Fege (DE19920114A1 ), Nov. 9, 2000, Claims of DE19920114, p. 1.*

PCT International Search Report for PCT/US03/41560, Applicant: Quiescence Medical, Inc., Forms PCT/ISA/210 and PCT/ISA/220, dated Oct. 4, 2004, 4 pages.

European Patent Office, Office Action for related EP Patent Application No. 03800323.2-2310, May 14, 2007, 5 pages.

Office Actions and Applicant Responses for related U.S. Appl. No. 11/126,649, 59 pages.

Office Actions and Applicant Responses for related U.S. Appl. No. 10/748,761, 35 pages.

* cited by examiner

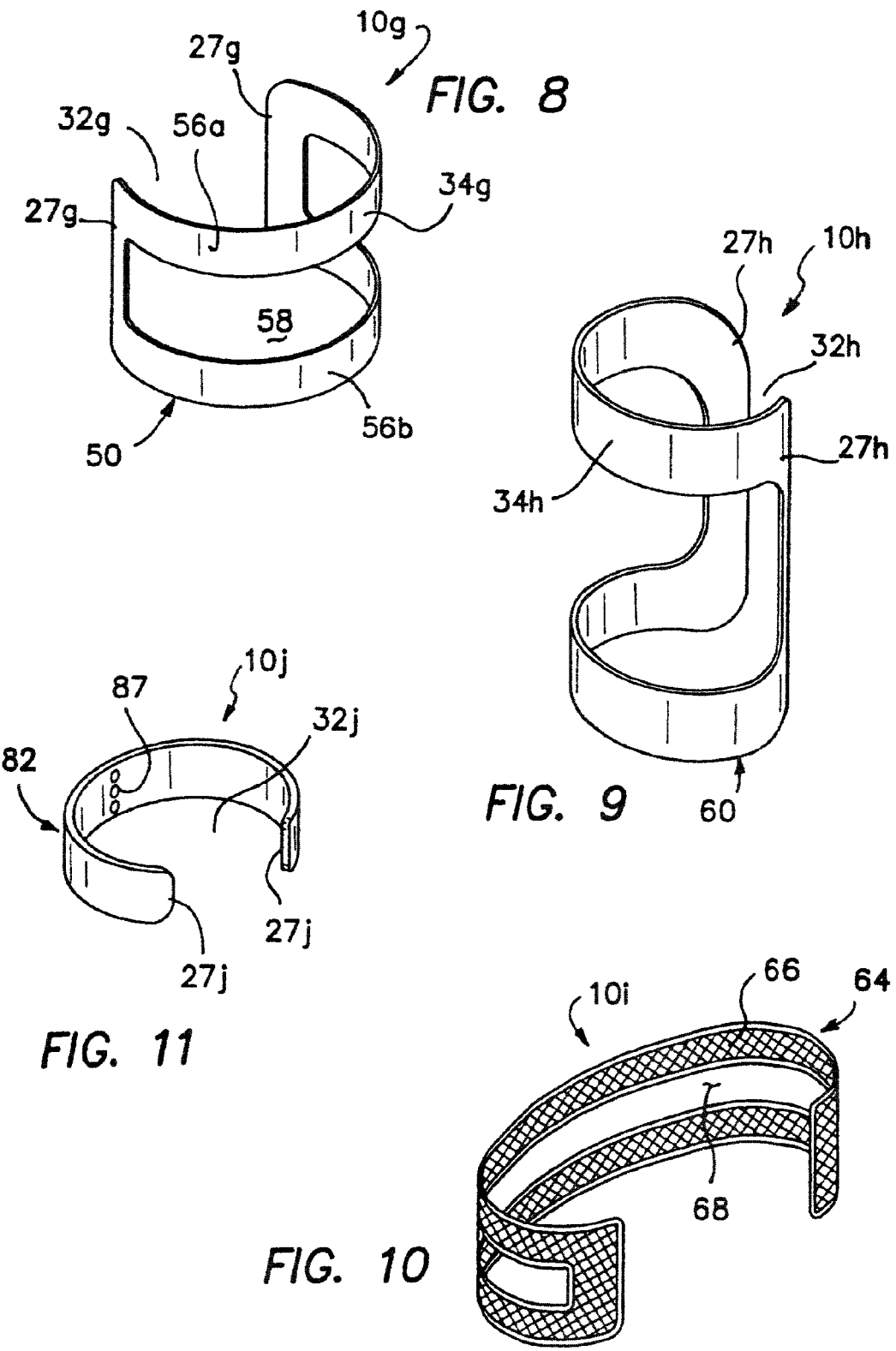

ial health,
APPARATUS AND METHODS FOR TREATING SLEEP APNEA

RELATED APPLICATIONS

This application is a continuation of co-pending application Ser. No. 10/541,255, filed Mar. 27, 2006, which is a continuation-in-part of U.S. patent application Ser. No. 10/624,915 filed on Jul. 22, 2003 which claims the benefit of U.S. provisional application Ser. No. 60/436,945 filed on Dec. 30, 2002, and U.S. provisional application Ser. No. 60/437,058 filed on Dec. 30, 2002, the disclosure of each of which is incorporated in its entirety herein by this specific reference.

BACKGROUND OF THE INVENTION

The present invention generally relates to apparatus and methods for treating sleep apnea and/or related breathing disorders, and more specifically relates to apparatus for placement in the oropharyngeal region of a human or animal and methods using such apparatus for treating sleep apnea and/or snoring.

Sleep apnea is a sleep-related breathing disorder that is thought to affect between 1-10% of the adult population. Recent epidemiologic data indicate that 2% of women and 4% of men between the ages of 30 and 60 years meet the minimum diagnostic criteria for sleep apnea syndrome, representing more than 10 million individuals in the United States. It is a disorder with significant morbidity and mortality, contributing to increased risk of hypertension, cardiac arrhythmias, stroke, and cardiovascular death. Another common sleep-related breathing disorder is snoring, which may be associated with or independent of sleep apnea.

The present invention has been developed to aid in the treatment of snoring and/or the various degrees of hypopnea and apnea that occur due to pathological disturbances in the sleep process. One of the main reasons of the sleep disturbance is the relaxation of the tongue and pharyngeal walls to varying degrees during the several stages of sleep. When fully awake, these tissues have normal tone as air passes in and out of the lungs during respiration. However, during sleep, the musculature supporting these tissues relaxes. As air is inspired, the tongue and posterior walls of the pharynx collapse, causing snoring or more seriously, causing partial or complete obstruction of the airway.

Obstructive sleep apnea occurs due to a collapse of soft tissue within the upper airway during sleep. The ongoing force of inspiration serves to generate increasingly negative pressure within the pharynx, causing further collapse. The lack of respiration results in inadequate blood oxygenation, and rising carbon dioxide levels. The cardiovascular response produces an increase in the blood pressure and pulse. Cardiac arrhythmias often occur. The carbon dioxide increase and oxygen desaturation triggers a transition to a lighter sleep stage, usually without wakefulness. This transition brings a return to tonicity of the muscles of the upper airway, allowing normal breathing to resume. The person then returns to deeper stages of sleep and the process is repeated. The disease is quantified in terms of respiratory disturbances per hour. Mild disease begins at ten per hour, and it is not uncommon to find patients with indices of about one hundred or more.

Not surprisingly, sleep is extremely fragmented and of poor quality in persons suffering from sleep apnea. As a result, such persons typically feel tired upon wakening and may fall asleep at inappropriate times during the day. All aspects of quality of life, from physical and emotional health, to social functioning are impaired by obstructive sleep apnea.

Continuous Positive Airway Pressure ("CPAP"), disclosed for example in U.S. Pat. No. 5,065,756, is a popular non-surgical treatment for patients suffering from sleep apnea. The disclosure of this patent is incorporated in its entirety herein by reference. CPAP is administered by means of a mechanical unit that delivers pressurized room air to the nasal passage, or airway, through a nose mask that is worn by the patient during sleep. Pressurized air enters from the CPAP unit through the nose when a person is sleeping, and opens the airway from the inside almost as if the air were an internal splint. The correct pressure for the individual is determined in a sleep laboratory. If the nasal airway will admit the flow of air, CPAP has in many cases offered immediate relief. Unfortunately however, compliance with, and long-term acceptance of this treatment are generally poor. Studies have shown that between 20% and 50% of patients fail to use nasal CPAP as prescribed. Problems associated with CPAP include excessive dryness of the mouth and throat, mucous congestion, sinusitis, and rhinorrhea. Breathing against positive air pressure is also discomforting to many patients.

Other non-surgical treatments for sleep apnea include the use of tongue retaining devices and other oral appliances that hold and/or pull the tongue or jaw in a forward position to open the airway by reducing collapse of the soft palate and/or tongue. These devices also suffer from poor compliance rates, and are usually associated with degenerative changes in the temporomandibular joint.

Surgical procedures have been proposed and practiced for the treatment of moderate to severe sleep apnea. Uvulopalatopharyngoplasty ("UPPP") is a surgical procedure used to treat obstructive sleep apnea. In UPPP, any remaining tonsillar tissue and a portion of soft palate is removed. The procedure increases the width of the airway at the throat opening. However, UPPP does not address apnea caused by obstructions deeper in the throat and airway, for example, apnea resulting from collapse of tissue near the base of tongue or in the oropharyngeal region of the airway.

LAUP, or Laser-Assisted Uvulopalatoplasty, is a modification of the above-mentioned technique, but has not proven particularly useful for sleep apnea. These surgical techniques are extremely invasive, requiring general anesthesia, and a prolonged, painful recovery.

Radio frequency tissue ablation (RFTA) with the trade name "Somnoplasty," has been used to shrink the soft palate, uvula and reduce tongue volume in the treatment of snoring and obstructive sleep apnea. Somnoplasty utilizes a radiofrequency tool that generates heat to create coagulative lesions at specific locations within the upper airway. The lesions created by the procedure are naturally resorbed in approximately three to eight weeks, reducing excess tissue volume and increasing the airway opening. Like UPPP and LAUP, more than one session is typically required and it does not address sleep apnea resulting from tissues deeper in the throat than the upper airway.

Another area of surgical interest lies in techniques designed to pull the tongue anteriorly. The most recent such surgical system designed to treat snoring (as well as obstructive sleep apnea) was approved by the FDA in February 1998. Known as the tongue suspension procedure (with the trade name Repose), it is intended to pull the tongue forward, thereby keeping the tongue from falling into the airway during sleep. The system utilizes a bone screw inserted into the mandible. The screw attaches to a non-absorbable suture which travels the length of the tongue and back. Similarly, the hyoid bone can be drawn anteriorly with two distinct screws, also attached to the mandible.

Techniques have also been developed for treating, specifically, the condition of snoring. Conrad et al., U.S. Pat. No. 6,250,307 discloses a method for treating snoring of a patient, which includes embedding an implant into a soft palate of a patient in order to alter a dynamic response of a soft palate to airflow. The methods of Conrad et al. are specifically designed to reduce the audibility of snoring but do not address the more serious condition of sleep apnea.

These conventional devices and treatments continue to suffer poor cure rates. The failures lie in their inability to maintain patency in the retropalatal region and retroglossal region (the caudal margin of the soft palate to the base of the epiglottis). The poor success rates combined with high morbidity, contribute to an ongoing need for more effective treatments for sleep apnea and/or snoring.

SUMMARY OF THE INVENTION

Accordingly, the present invention provides apparatus and methods effective to treat, for example, to substantially eliminate or at least reduce the occurrence of, sleep apnea and/or snoring, meaning to include snoring and/or other sleep-related breathing disorders. The apparatus and methods are relatively straightforward to structure and use, are minimally invasive and provide substantial benefits over conventional techniques in controlling sleep apnea and/or snoring.

In one broad aspect, the present invention provides apparatus comprising an appliance sized and structured to be permanently (that is, for long term usage or for a relatively long time, such as at least about 1 week or about 1 month, preferably at least about 6 months, more preferably at least about 1 year, even more preferably about 5 years or longer) or temporarily implanted or placed in an oropharyngeal region of a human or animal The present apparatus may comprise any material or materials suitable for placement in the pharyngeal region which are effective to stiffen, reinforce and/or strengthen tissues of the region in order to provide support to these tissues against collapse such that a patient can breathe more effectively than the patient would breathe without the material or materials placed in the region.

In one embodiment of the invention, the apparatus generally comprise an appliance sized and structured to be placed in a given position in the oropharyngeal region, other than to facilitate a surgical procedure, and to be effective, when placed in the given position, to treat sleep apnea and/or snoring in a human and or animal (hereinafter, sometimes "patient"). In addition, the appliance is structured to be effective, when so placed, to provide at least one additional benefit relative to a different device that is sized and structured for placement in a position in the patient other than in the given position in the oropharyngeal region. Preferably, the appliance is structured to provide an enhanced compliance with normal, healthy functioning of the oropharyngeal region of a patient relative to such a different device, for example, a stent that is not specifically structured to be utilized for treatment of sleep apnea. For example, the apparatus is structured to have an enhanced, relative to such a different device, ability to be tolerated, preferably comfortably tolerated, by the human or animal while the apparatus is in the given position in the oropharyngeal region, such as when the human or animal is awake or is naturally sleeping.

The appliance of the present invention is advantageously structured to have an enhanced, relative to such a different device, ability to provide support against collapse of the oropharyngeal region during natural sleep, as well as to allow proper closure of an airway in the oropharyngeal region during swallowing.

Preferably, the appliance is sized and structured so that, when so placed in the given position in the oropharyngeal region, the appliance is located substantially entirely within the pharyngeal region including, preferably, the oropharyngeal region. The apparatus is sized and structured to be temporarily placed in the given position or to be placed in the given position on a relatively long term basis for example, as described elsewhere herein. In addition, the appliance is preferably structured to resist migration within the oropharyngeal region or outside the oropharyngeal region.

In one embodiment of the invention, the appliance comprises a substantially flat or planar member, when located outside the body in a resting or at rest position, including spaced apart end portions and a body portion joining the end portions. In this embodiment of the invention, the apparatus preferably is designed such that when the apparatus is appropriately positioned in the given position, the appliance takes on a curved configuration with end portions bearing against and supporting against collapse, the lateral walls of the oropharyngeal region. The appliance may be sized and structured such that when the apparatus is appropriately placed in the given position, the end portions are spaced apart anteriorly of the posterior wall of the oropharyngeal region, for example, by a portion of the anterior wall of the oropharyngeal region. Preferably, the appliance expands to form an effective diameter of about 32 mm or greater in order to adequately expand to fill the oropharyngeal region.

In some embodiments of the invention, the apparatus may be structured to facilitate removal thereof from the oropharyngeal region. For example, the apparatus may be structured such that when the apparatus is in other than the deployed configuration, for example, when the apparatus is located outside an oropharyngeal region of a human or animal or outside the body of the human or animal in a resting position, the appliance comprises a member that has a flexibility and resiliency that allows the appliance to be folded, rolled or coiled to take on a relatively smaller radius for facilitating insertion and/or removal thereof into or from the oropharyngeal region, for example, through the mouth or oral cavity of the patient. When introduced and released into the pharyngeal region, the appliance unfolds, unrolls or uncoils, and provides pressure against one or more portions of the pharyngeal region, providing support thereto and maintaining or achieving patency of the pharyngeal region, for example, whether the patient is awake or is naturally sleeping.

The appliance is preferably sized and structured to allow substantially natural functioning of the oropharyngeal region and the epiglottis when the appliance is located in the given position in the pharyngeal region of the patient.

It will become apparent that various configurations of the apparatus are possible to achieve one or more of the benefits of the present invention in treating, e.g. controlling, sleep apnea and/or snoring, and it is to be appreciated that each of such various configurations, for example, the herein disclosed various configurations and modifications thereof, are considered to be within the scope of the present invention. Such configurations include, but are not limited to, an appliance having a substantially elliptical configuration, a substantially circular configuration, a substantially rectangular configuration, a substantially cylindrical configuration, a substantially linear configuration, a substantially cross-shaped configuration, a substantially C-shaped configuration, a substantially cuff shaped configuration, a substantially coil shaped configuration and the like configurations and combinations thereof. For example, in a more specific embodiment of the invention, the appliance comprises, in a rest position outside the body of a human or animal a substantially, flat, flexible, elliptical member having rounded end portions, a length defined between the end portions, and a body portion comprising a plurality of spaced apart struts extending along at least a substantial portion of the length between the end portions.

Preferably, the appliance, when located in the oropharyngeal region, has a resiliency and flexibility, for example, resiliency and/or flexibility in at least one direction or at least two different directions or at least three different directions, that enables the appliance to provide an appropriate amount of support and reinforcement to oropharyngeal tissues during natural sleep, while enabling substantially normal functioning of the oropharyngeal region and the epiglottis, for example, during swallowing.

In some embodiments of the invention, the apparatus comprises an appliance sized and structured to be placed within the pharyngeal region of the patient and, when so placed, having an intrinsic ability to maintain patency of the pharyngeal region during natural sleep of the patient.

For example, the appliance may be structured to cause a reduced fibrotic reaction when placed in the pharyngeal region relative to a similar appliance that is structured from materials that will cause a fibrotic response, for example relative to a similar appliance that is made of polyester.

In some embodiments of the invention, the appliance having said intrinsic ability to maintain patency is structured to have smooth, radiused edges and smooth surfaces, for example in order to inhibit a fibrotic reaction of tissues when the appliance is placed in the pharyngeal region.

In some embodiments of the invention, the appliance is structured to cause the substantially no fibrotic reaction when placed in the pharyngeal region.

The appliance preferably comprises an elastic material. More preferably, the appliance comprises a super-elastic material. A number of suitable elastic and super-elastic materials are well known and can be employed in the present apparatus. One particularly useful material is metallic material, or metal, for example a super-elastic metal such as a nickel titanium alloy, known as Nitinol. The appliance preferably has a hoop strength effective to support the oropharyngeal region against collapse during natural sleep. More preferably, the appliance has a hoop strength in a range of at least about 5 cm water to about 400 cm water or greater.

The apparatus advantageously comprises an appliance sized and structured to be placed in a position in the oropharyngeal region in proximity to the epiglottis, other than to facilitate a surgical procedure, effective in treating sleep apnea and/or snoring. The appliance is sized and structured to substantially entirely fit within the oropharyngeal region when placed in position. A portion of the device may also be considered to extend above the oropharyngeal region along the posterior portion of the pharynx.

In another broad aspect of the invention, the apparatus for treating sleep apnea and/or snoring comprises an element placed within the oropharyngeal region that is effective, when so placed, to stiffen, reinforce and/or strengthen tissues within the oropharyngeal region in order to support these tissues against collapse and allow substantially normal breathing during sleep.

For example, the element may comprise at least one strip of material that is structured to be placed within the walls of the pharyngeal region. For example, the element may comprise multiple strips of material, such as multiple strips of metal, that are structured and suitable to be implanted within the oropharyngeal tissues, for example, beneath the mucosal tissue. In other words, such strips of material are structured and are suitable for submucosal placement within the walls of the pharyngeal region. To illustrate this feature of the invention, the element may comprise multiple strips of the same or different sizes and/or dimensions that are suitable for implantation in a spaced apart arrangement. For example, the multiple strips may be implanted in a generally horizontal fashion, that is, with the patient in the supine position, generally parallel to the length or longitudinal axis of the patient's body.

In a related aspect of the invention, a method for treating sleep apnea and/or snoring comprises the steps of securing one or more elements to the pharyngeal region and allowing the elements to provide an opening force against the pharyngeal walls, such opening force being sufficient to reinforce the walls against collapse during natural sleep while allowing substantially normal functioning of the oropharyngeal region.

Preferably the method comprises placing at least partially submucosally, within the pharyngeal region of a patient, an appliance effective, when so placed, to maintain patency of the pharyngeal region.

Preferably, the step of placing comprises placing the apparatus substantially entirely submucosally, preferably in the oropharyngeal region.

The apparatus, in accordance with an especially advantageous embodiment of the invention, is sized to be placed, at least partially, circumscribing an interior hollow passage defined by the pharyngeal region, for example the oropharyngeal region. In a related aspect of the invention, the appliance is sized to be placed circumscribing, at least once, the interior hollow passage defined by the pharyngeal region.

In another embodiment of the invention, the element may comprise an element that provides a magnetic opening force against collapsing pharyngeal, for example, oropharyngeal, tissues. For example, the element may comprise an appliance, such as described and shown elsewhere herein, that is at least partially magnetized. More specifically, the element may comprise two or more magnetic elements having like poles facing one another, to create a magnetic field that can be utilized to provide a useful opening force to the pharyngeal, for example, oropharyngeal, region.

In another embodiment of the invention, the apparatus comprises an element that includes a transverse portion sized and structured to provide an opening force to the pharyngeal region and at least one longitudinal portion depending from the transverse portion, for example from an end of the transverse portion. The transverse portion may have a substantially bow or curved shape, or may be straight and planar. The longitudinal portion is structured to be placed substantially submucosally within the pharyngeal region, for example, extending downward from the transverse portion and aligned along a longitudinal axis of the pharyngeal region.

The at least one longitudinal portion may comprise two or more longitudinal portions, depending from and spaced apart by the transverse portion. In one aspect of the invention, the longitudinal portions comprise two longitudinal portions depending from each end of the transverse portion. In this embodiment of the invention, the element has a substantially U-shaped configuration.

In yet another embodiment of the invention, the appliance includes at least one element having a substantially bow shaped, substantially linear configuration and being sized and structured to be placed at least partially submucosally within the walls of the pharyngeal region in a position transverse to a longitudinal axis of the pharyngeal region. The at least one element may comprise a plurality of said elements having substantially bow shaped, substantially linear configurations, such that a plurality of the elements may be placed at spaced apart intervals within the walls of the pharyngeal region.

In some embodiments of the invention, the apparatus comprises a component which has a length and a thickness smaller than the length and, which when placed into the pharyngeal region, extends a longitudinal distance, along the pharyngeal region, a distance further than or greater than the thickness of the component.

Methods for treating sleep apnea and/or snoring in a human or an animal having an oropharyngeal region are provided. In one aspect of the invention, the methods generally comprise providing an appliance, such as described elsewhere herein, in the oropharyngeal region of the human or animal The appliance, located in the oropharyngeal region, is effective in treating sleep apnea and/or snoring during natural sleep of the human or animal In one embodiment, the step of providing includes placing an appliance in the oropharyngeal region that is effective in maintaining patency of the oropharyngeal region during natural sleep of the human or animal Preferably, the appliance is effective in maintaining patency without causing substantial interference with one or more natural functions of the oropharyngeal region or the epiglottis. For example, the appliance may be structured, when placed in the pharyngeal region, to be effective to support the tissues of the oropharyngeal region against collapse while allowing the oropharyngeal region to close and/or otherwise function consistent with normal swallowing. The apparatus is designed so that, when the appliance is placed in the pharyngeal region it is effective in supporting and holding the lateral walls of the oropharyngeal region in an open position, and/or in supporting and holding the tongue of the patient in a forward position, for example, during natural sleep of the patient.

In yet another embodiment of the invention, a method is provided for maintaining patency of a pharyngeal region of a human or an animal during natural sleep. The method generally comprises the steps of providing a member in a substantially flat or precurved configuration, the member having a body portion and end portions spaced apart by the body portions, and implanting the member, at least partially submucosally, within the pharyngeal region.

Advantageously, the member is effective to provide a substantially constant force against at least a portion of each of a right and left lateral wall of the pharyngeal region.

For example, the step of implanting comprises implanting the member into pharyngeal region such that the member is substantially entirely submucosally implanted therein.

In yet another embodiment of the invention, a method for maintaining patency of a pharyngeal region of a human or animal during natural sleep and for purposes other than surgery is provided wherein, the method generally comprises the steps implanting an appliance that is structured to intrinsically cause or maintain patency of the pharyngeal region when implanted therein. This is distinguished from a method of the present invention for treating a patient which comprises a step of causing a tissue reaction of a pharyngeal region of the patient, said tissue reaction being effective in at least one of strengthening and stiffening lateral walls of the pharyngeal region. For example, in an alternative embodiment of the invention, the method comprises strengthening the walls of the oropharyngeal region by, for example, causing a tissue reaction, for example, by applying an active agent to the walls of the pharyngeal region or, for example, placing at least one member into the lateral walls to cause a tissue reaction.

Preferably, the step of providing may include inserting the appliance into the oropharyngeal region, for example through the mouth or oral cavity of the patient, or alternatively, through the nasal cavity of the patient, while the appliance is in a first configuration and, thereafter, allowing the appliance to reconfigure to a second configuration within the oropharyngeal region.

In yet another aspect of the invention, a method for treating sleep apnea and/or snoring may comprise causing a tissue reaction in an oropharyngeal region of a patient. Such tissue reaction is effected to cause sufficient stiffening and/or strengthening of targeted oropharyngeal tissues in order to substantially reduce the occurrence of collapse of those tissues during natural sleep of the patient.

For example, the step of causing a tissue reaction may comprise one of injecting a suitable agent into the tissues, applying wave energy to the tissues and/or causing mechanical irritation to the tissues in order to provoke a strengthening response.

Each and every feature described herein, and each and every combination of two or more of such features, is included within the scope of the present invention provided that the features included in such a combination are not mutually inconsistent.

These and other aspects of the present invention are apparent in the following detailed description and claims, particularly when considered in conjunction with the accompanying drawings in which like parts bear like reference numerals.

BRIEF DESCRIPTION OF THE DRAWINGS

FIGS. 7, 8, and 9 show, in perspective view, various other embodiments of the invention comprising substantially cuff-shaped appliances of different proportions to accommodate different patient needs.

FIG. 10 shows a perspective view of still another embodiment of the invention comprising a substantially cuff shaped embodiment comprising a mesh material.

FIG. 11 a perspective view shows a yet further embodiment of the invention comprising a substantially solid C-shaped appliance having apertures for allowing tissue ingrowth.

FIG. 29A shows a simplified perspective view of an embodiment of the invention similar to the embodiment shown in FIG. 29, in which the transverse portion is sloped downwardly with respect to the longitudinal portions.

FIG. 30A shows a magnified view of a portion of the apparatus circumscribed by line A of FIG. 30.

FIG. 30B shows a magnified view of a portion of the apparatus circumscribed by line B of FIG. 30.

FIG. 30C shows a side view of the apparatus of FIG. 30.

DETAILED DESCRIPTION OF THE INVENTION

Figure 1:
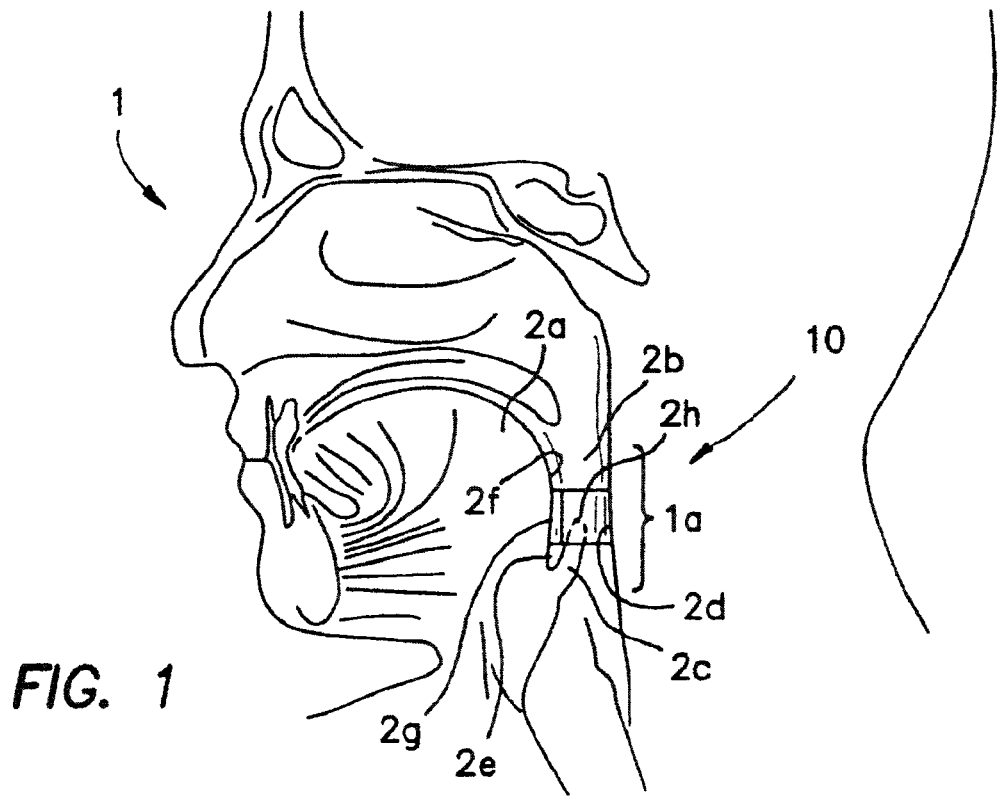
FIG. 1 shows a side view of an apparatus of the present invention positioned in an oropharyngeal region of a patient (shown in cross-section for clarity).

In a broad aspect of the invention, the apparatus generally comprise an appliance sized and structured to be placed in a given position in an oropharyngeal region of a human or animal patient, other than to facilitate a surgical procedure on said patient, and being effective in treating sleep apnea and/or snoring of said patient. The appliance is further effective, when so placed in the given position, to provide at least one additional benefit or advantage relative to a device sized and structured for placement in a different position in a human or animal wherein a "different position" is defined as a position other than the given position.

Incorporated herein by this specific reference is the entire disclosure of each of the following patents:

Fraser et al. U.S. Pat. No. 5,571,135, Turnland U.S. Pat. No. 5,360,401, Winston et al. U.S. Pat. No. 5,306,294, Heyn et al. U.S. Pat. No. 5,201,757, Burton et al. U.S. Pat. No. 5,078,720, Termin et al. U.S. Pat. No. 5,071,407, Porter U.S. Pat. No. 5,064,435, Wallsten et al. U.S. Pat. No. 5,061,275, Burton et al. U.S. Pat. No. 5,026,377, Savin et al. U.S. Pat. No. 4,950,227, Imbert U.S. Pat. No. 4,875,480, Wallsten et al. U.S. Pat. No. 4,848,343, Wallsten et al. U.S. Pat. No. 4,732,152, Garza et al. U.S. Pat. No. 4,665,918, Gould et al. U.S. Pat. No. 4,572,186, Strecker U.S. Pat. No. 6,485,524 B2, Klumb et al. U.S. Pat. No. 6,488,700 B2, Klumb et al. U.S. Pat. No. 6,248,122 B1, Klumb et al. U.S. Pat. No. 6,238,430 B1, Harada et al. U.S. Pat. No. 5,037,427, McNamara et al. U.S. Pat. No. 5,147,370, Kolobow et al. U.S. Pat. No. 6,027,516, Thorud et al. U.S. Pat. No. 6,019,779, Holman U.S. Pat. No. 5,980,533, St. Germain U.S. Pat. No. 5,836,966, Klein U.S. Pat. No. 5,797,952, Gunderson U.S. Pat. No. 5,776,142, Summers et al. U.S. Pat. No. 5,772,668, Lukic et al. U.S. Pat. No. 5,709,703, Lenker et al. U.S. Pat. No. 5,683,451, Bergentz et al. U.S. Pat. No. 3,993,078, Myler et al. U.S. Pat. No. 5,474,563, Limon U.S. Pat. No. 5,476,505, St. Germain et al. U.S. Pat. No. 5,534,007, Roberts et al. U.S. Pat. No. 5,603,698, Boatman et al. U.S. Pat. No. 5,632,771, Myler et al. U.S. Pat. No. 5,643,309, Strecker U.S. Pat. No. 6,485,524 B2, Augustine et al. U.S. Pat. No. 6,427,686 B2, Linder U.S. Pat. No. 5,664,567, Downing U.S. Pat. No. 4,821,715, Alfery U.S. Pat. No. 6,386,199 B1, Lane et al. U.S. Pat. No. 5,494,029, Grosbois et al. U.S. Pat. No. 6,474,339 B1, Bullard U.S. Pat. No. 5,791,341, Gianturco U.S. Pat. No. 4,580,568, Hart U.S. Pat. No. 5,950,624, Zammit U.S. Pat. No. 6,328,753 B1, Woodson U.S. Pat. No. 6,161,541, Mark et al. U.S. Pat. No. 6,419,641 B1, Thompson et al. U.S. Pat. No. D458,679 S, Beyar et al. U.S. Pat. No. 6,371,979 B1, Beyar et al. U.S. Pat. No. 6,371,953 B1, Thompson U.S. Pat. No. 6,358,274 B1, Klima et al. U.S. Pat. No. 6,273,876 B1, Thompson U.S. Pat. No. 6,254,631 B1, Thompson U.S. Pat. No. 6,132,461, Thompson U.S. Pat. No. 6,132,460, Vidlund U.S. Pat. No. 6,110,164, Beyar et al. U.S. Pat. No. 6,090,115, Vidlund et al. U.S. Pat. No. 6,033,394, Donadio, III U.S. Pat. No. 6,027,863, Johnson et al. U.S. Pat. No. 6,022,343, Thorud et al. U.S. Pat. No. 6,019,779, Dustrude et al. U.S. Pat. No. 5,911,752, Clubb et al. U.S. Pat. No. 5,815,904, Eliachar et al. U.S. Pat. No. 5,048,518, Conrad et al. U.S. Pat. No. 6,450,169, Bibi U.S. Pat. No. 6,371,112, Thornton U.S. Pat. No. 6,325,064, Thornton U.S. Pat. No. 6,305,376, Thornton U.S. Pat. No. 6,374,824, Dutkiewicz U.S. Pat. No. 6,257,236, Rittmann U.S. Pat. No. 6,270,512, Thorner U.S. Pat. No. 6,238,411, Hurbis U.S. Pat. No. 6,106,541, Lundy, Jr. et al. U.S. Pat. No. 6,098,616, Muchin U.S. Pat. No. 6,058,931, Filis U.S. Pat. No. 6,004,342, Christopher U.S. Pat. No. 5,954,050, Boussignac U.S. Pat. No. 6,363,935, Muchin U.S. Pat. No. 5,718,224, Conrad et al. U.S. Pat. No. 6,250,307, Conrad et al. U.S. Pat. No. 6,401,717, Conrad et al. U.S. Pat. No. 6,390,096, Berthon-Jones U.S. Pat. No. 6,123,082, Halstrom U.S. Pat. No. 6,161,542, Halstrom U.S. Pat. No. 5,868,138, Tielemans U.S. Pat. No. 6,408,852, Shapiro U.S. Pat. No. 5,117,816, Bergersen U.S. Pat. No. 6,129,084, Edwards et al. U.S. Pat. No. 6,126,657, Edwards U.S. Pat. No. 5,800,379, Edwards U.S. Pat. No. 5,738,114, Rotramel U.S. Pat. No. 6,171,314, Anderson U.S. Pat. No. 5,893,365, Thomas U.S. Pat. No. 5,988,170, Gaumond et al. U.S. Pat. No. 6,379,311, Belfer U.S. Pat. No. 6,092,523, Richmond et al. U.S. Pat. No. 6,345,202, Meyer et al. U.S. Pat. No. 6,329,352, Estes et al. U.S. Pat. No. 5,970,975, Bourgeois et al. U.S. Pat. No. 6,126,611, Samelson U.S. Pat. No. 4,304,227, Dror U.S. Pat. No. 4,198,967, Gardy U.S. Pat. No. 4,676,240, Meade U.S. Pat. No. 5,682,903, Alvarez et al. U.S. Pat. No. 5,649,540, Parks U.S. Pat. No. 5,642,737, Hilsen U.S. Pat. No. 5,611,355, Zammit U.S. Pat. No. 6,183,493, Eliachar U.S. Pat. No. 4,794,924.

It has been discovered that a number of the devices disclosed in the above referenced patents, that are conventionally utilized or suggested for utilization in body regions other than the oropharyngeal region and/or to treat conditions other than sleep apnea and/or snoring, can be utilized or modified to be utilized in the oropharyngeal region of a human or an animal in order to treat sleep apnea and/or snoring, in accordance with the present invention. Any such modification or modifications to such conventional devices are considered to be included within the scope of the apparatus of the present invention. In addition, the use of any of such previous devices, and any modified such previous devices, in the oropharyngeal region of a human or an animal in order to treat sleep apnea and/or snoring is considered to be within the scope of the methods of the present invention. It can be noted that currently there are no vascular or other stents marketed for use in natural body conduits which are designed to expand to diameters in excess of 32 mm.

For example, the at least one additional benefit or advantage of the apparatus of the present invention, relative to a device conventionally utilized or suggested for utilization in body regions other then the oropharyngeal region and/or to treat conditions other than sleep apnea and/or snoring, may comprise, without limitation, at least one or more of the following: the apparatus is structured to be located in the oropharyngeal region and to have an enhanced ability to be tolerated by the human or animal, for example, while the human or animal is awake or is naturally sleeping; the apparatus is structured to provide enhanced resistance to static collapsing forces of the oropharyngeal region and/or hypopharynx; the apparatus is structured to have an enhanced ability to allow for dynamic collapse; the apparatus is structured to have enhanced non-mobility, for example, upon coughing, throat clearing and/or sneezing; the apparatus is structured to have enhanced conformity to the healthy, normal shape of the pharynx; the apparatus is structured to have an enhanced ability to be removable; the apparatus is structured to have an enhanced ability to be deployable under direct vision via nasopharyngoscopy/laryngoscopy; and the like benefits.

In addition, the present apparatus preferably are structured to not substantially interfere with swallowing, respiration, vocalization, mucociliary function, epiglottis functioning and the like. For example, in some embodiments of the invention, the apparatus is structured to be substantially aligned along and longitudinally with the oropharyngeal walls. The present apparatus are structured to maintain the openness of the pharyngeal region during natural sleep.

Turning now to FIG. 1, a cross-sectional anatomical view of a human patient 1 is shown. The patient 1 has apparatus 10 in accordance with the present invention located within the patient's oropharyngeal region 1a in order to treat, for example, control, reduce or even eliminate, the occurrence of sleep apnea and/or snoring Snoring and sleep apnea are often caused by a combination of narrowness and low muscle tone of the upper airways. The tongue 2a falls back and may obstruct the airway, possibly leading to an arousal reaction and disturbing the normal sleeping pattern. Other portions of the oropharyngeal region may also collapse. For example, the lateral walls 2b of the oropharyngeal region often become excessively lax and block a free flow of air during respiration. When the patient 1 is supine, for example, when the patient 1 is asleep and lying on his/her back, the relaxed tongue 2a moves inferior (down) and posterior (back), and/or the lateral walls 2b of the oropharyngeal region collapse inwardly resulting in a narrower pharynx relative to when the patient 1 is upright. One cause for the narrowing of the pharynx in the supine position could be that the oropharyngeal region 1a and hypopharyngeal region 1b, which have low consistencies, collapse because of lack of direct hard tissue support.

The apparatus 10 may be secured to the pharyngeal region by various means. For example, the apparatus 10 may be sutured to the pharyngeal region, for example with dissolvable sutures that will allow the apparatus 10 to be held in place while the apparatus 10 becomes fixed to the region by means of tissue ingrowth. Alternatively, the apparatus 10 may be secured to the region by means of a suitable biocompatible adhesive as are presently known in the art. Alternatively still, the apparatus 10 may be secured to the region by being surgically implanted into the region, for example, directly beneath the region's mucosal layer, (hereinafter, "submucosally"), for example, by being pulled, with a surgical needle for example, into and beneath the mucosal layer such that the apparatus at least partially circumscribes the region.

The apparatus 10 of the present invention is preferably designed to provide direct support to at least some of these tissues when the patient 1 is supine and asleep. For example, the apparatus 10 of the present invention is structured so that when placed in the given position in oropharyngeal region 1a, the apparatus 10 will push the tongue forward, and/or push the lateral walls 2b away from one another thereby holding the airway patent or open during the time the human or animal is naturally sleeping.

As shown, the apparatus 10 may be sized and structured to be positioned adjacent the epiglottis 2c of patient 1, but preferably not in contact therewith. For example, in one embodiment of the invention, the apparatus 10 is designed to overlay a posterior wall 2d of the oropharyngeal region 1a and provide an opening force outwardly against opposing lateral walls 2b of the oropharyngeal region 1a. In other embodiments of the invention, the apparatus 10 is designed to rest within a valecullar space 2e and provide a pushing force against the base 2f of the tongue 2a which makes up a portion of the anterior wall 2g of the oropharyngeal region 1a. The valecullar space 2e, as the term is used herein, is defined as being the space between the anterior wall 2g of the throat and the upper tip 2h of the epiglottis 2c down to the conjunction of the epiglottis 2c with the anterior wall 2g of the pharynx.

In any event, the apparatus 10 is designed in such a manner as to substantially prevent same from interfering with the normal functioning of the tissue around the apparatus 10, particularly with the normal functioning of the epiglottis 2c. The apparatus 10 may include structures (as described elsewhere herein) for anchoring or securing the apparatus 10 within the oropharyngeal region 1a in order to prevent the apparatus 10 from migrating away from or out of the given position.

Preferably, in all embodiments of the invention, the apparatus 10 is structured to closely and flexibly conform to the size and contours of at least a portion of the oropharyngeal region 1a.

In one useful embodiment, the apparatus 10 can be said to be effective to provide a support substantially equivalent to the support of tissue and/or muscles of an oropharyngeal region in a healthy, toned state.

As a specific example, the apparatus 10 may be sized and shaped to fit a human patient having a measured anterior-posterior linear distance between the pharyngeal walls, when the patient is awake and not supine, and the tongue and/or other tissues are not fully lax.

The apparatus 10 is preferably structured to maintain a radial force or pressure, for example, a substantially constant radial force or pressure, against the oropharyngeal region, specifically against the lateral walls of the oropharyngeal region, the posterior portion of the oropharyngeal region, and/or the base of the tongue. The pressure of the apparatus maintained against this region is advantageously sufficient to maintain patency of the oropharyngeal region during natural sleep in a supine position (for example, greater than about 10 cm of water), and preferably exerts pressure less than that exerted by the surfaces of the oropharyngeal region during swallowing (for example, about 400 cm of water). The apparatus preferably has a hoop strength in a range of about 5 cm water up to about 400 cm water. It is further noted that the design of apparatus 10 allows for variable hoop strength as measured along different points about the circumference of the appliance of the apparatus.

The present apparatus 10 is designed and structured to allow substantially normal functioning of the oropharyngeal and pharyngeal regions, while maintaining the structural integrity of the apparatus over a long period of time. An important consideration in the design of the present apparatus 10 includes the requirement that the apparatus 10 substantially maintain its structural integrity and strength despite the highly dynamic, peristaltic motion of the oropharyngeal and hypopharyngeal regions.

For example, it is known that a human being typically swallows an average of two times a minute, throughout the day. This equals around 2000 swallows per day. The force of the swallow varies from 1.5 lbs. to 6 lbs. of pressure, and the force lasts for about 0.1 to about 0.2 seconds.

Swallowing also includes the involuntary apposition of the soft palate to the posterior pharyngeal wall, which is believed to last almost a second and producing a pressure of about 160 millimeters of mercury and initiates pharyngeal peristalsis, i.e. the wavelike muscular contractions that move food along the alimentary canal in the pharyngeal region. This moving front of contraction passes through the pharyngeal constrictors in sequence, traversing the pharynx and hypopharynx at about 15 centimeters per second to reach the upper esophageal sphincter in about one second. The hypopharyngeal contraction lasts about 0.3 to about 0.5 seconds and generates an intraluminal pressure of 200 millimeters of mercury. The present invention is designed to flex and contract along with this wave-like motion of the various muscles in the oropharyngeal and hypopharyngeal region.

The appropriate amount of force necessary to provide adequate support to maintain patency and consistent air flow through the oropharyngeal region during sleep, while allowing for the dynamic motion of the pharyngeal region and normal function of the oropharyngeal region and/or hypopharyngeal region, may vary between patients. Therefore, preferably the apparatus 10 is available in a range of radial forces and sizes in order to suit different individuals.

Preferably, each of the embodiments of the apparatus in accordance with the present invention are made of resilient and elastic biocompatible materials, for example, one or more metals, and all edges and surfaces are smooth and free of sharp portions, burrs and contaminants. Such smooth, or at least substantially smooth, edges and surfaces are effective to reduce or inhibit fibrosis or other scar tissue formation in the pharyngeal region, which fibrosis or scar tissue formation can interfere with the dynamic motion or normal functioning of the pharyngeal region. In one embodiment of the invention, the present apparatus preferably is structured, for example is made of metal and/or has substantially smooth edges and surfaces, to substantially reduce, more preferably to substantially eliminate, fibrosis of other scar tissue formation. This is in contrast to the use of materials selected to promote of induce fibrosis of other scar tissue formation.

FIGS. 2-6 show various embodiments of the invention that are generally cylindrical or tubular in structure. Except as expressly described herein, each of the apparatus 10a, 10b, 10c, 10d and 10e, shown in FIGS. 2-6 respectively, is similar to apparatus 10 and is structured, unless otherwise noted herein, to be utilized for the treatment of sleep apnea and/or snoring as hereinabove noted.

Figure 2:
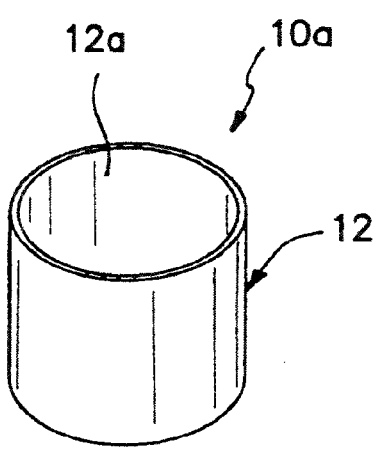
FIG. 2 shows a perspective view of an embodiment of the invention comprising a substantially solid walled cylindrical appliance.

Turning now specifically to FIG. 2, apparatus 10a is structured to fit substantially entirely within the oropharyngeal region and at least partially within the valecullar space and/or preferably extending no higher than the upper surface of the base of the tongue in the anterior portion of the apparatus. The posterior portion of the apparatus may be designed to provide additional support above the oropharyngeal region.

The appliance 12 defines a central open or hollow space 12a and can be made of any suitable biocompatible material, for example, stainless steel, other metals, or plastics (polymeric materials), and the like, and combinations thereof.

Figure 3:
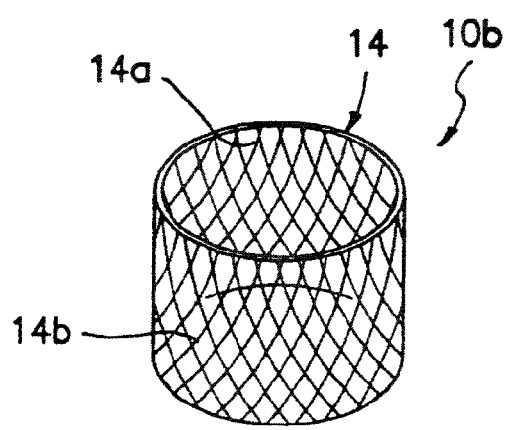
FIG. 3 shows a perspective view of another embodiment of the invention comprising a substantially mesh walled cylindrical appliance.

FIG. 3 shows an apparatus 10b in accordance with the present invention comprising a substantially cylindrical appliance 14 similar to appliance 12, with the most significant difference being that appliance 14 is comprised of a mesh, for example a woven metal wire mesh. The mesh appliance 14 defines a central open or hollow space 14a and preferably comprises wires 14b made of a super-elastic material, for example, a nickel titanium alloy (to be described in more detail elsewhere herein), such as the alloy known as Nitinol.

Figure 4:
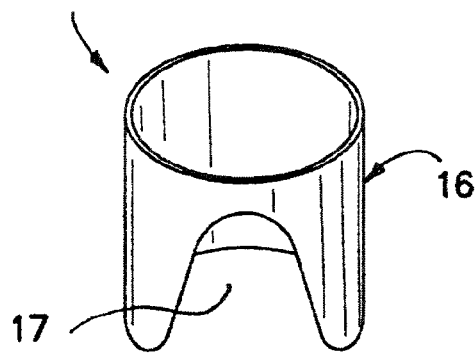
FIG. 4 shows a perspective view of an additional embodiment of the invention similar to the apparatus shown in FIG. 2, and including a recessed portion for accommodating an epiglottis of a patient.

FIG. 4 shows an additional apparatus 10c of the present invention, similar to apparatus 10a, comprising a solid cylindrical appliance 16 including a feature of a cut-out region 17 defined in the appliance 16, the cut-out region being appropriately sized, shaped, and positioned to accommodate natural movements and functions of the epiglottis of the patient. Thus, in this embodiment of the invention, apparatus 10c is fitted to a patient with cut-out portion 17 facing an anterior wall of the oropharyngeal region. The epiglottis is therefore free to move inwardly and outwardly of the appliance by means of the cut-out region.

Phantom lines in FIG. 4 illustrate another apparatus 10c' of the invention comprising an appliance 16' including longitudinal members 16a depending from a brace portion 16b. The brace portion 16b is structured to be secured partially circumferentially to the pharyngeal walls, with depending members 16a preferably being submucosally implanted within the pharyngeal walls. It is to be appreciated that although only four members 16a are shown, the appliance 10c' may include any other number of members, having the same or differing lengths, depending upon the needs of an individual patient.

Figure 5:
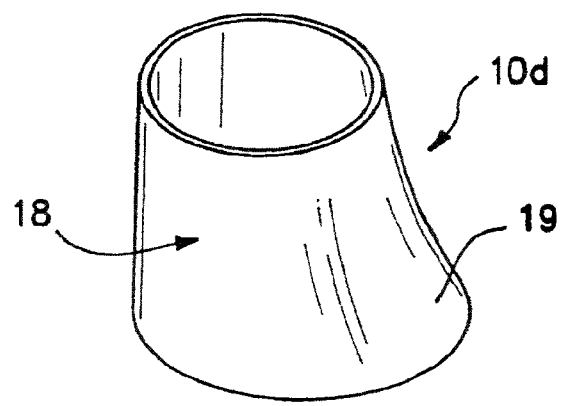
FIG. 5 shows a perspective view of yet another embodiment of the invention including an extended portion.

FIG. 5 shows yet another apparatus 10d of the present invention, comprising an appliance 18 having a relatively wider diameter distal or lower portion 19 which functions to anchor or hold the appliance 18 within the valecullar space. When in use, apparatus 10d is anchored at portion 19 within the vallecular space allowing the epiglottis to function normally within the relatively wider hollow area defined by the lower portion 19.

Figure 6:
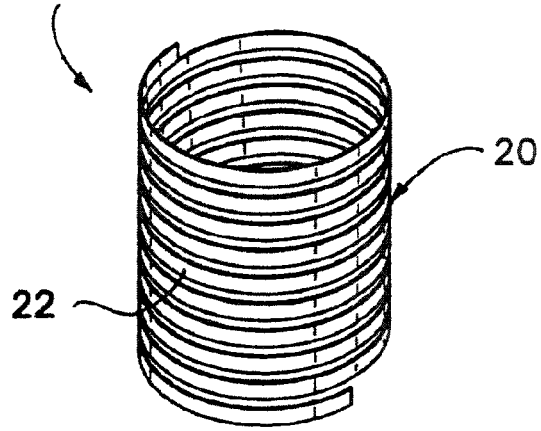
FIG. 6 shows a perspective view of a further embodiment of the invention comprising a coiled appliance.

FIG. 6 shows a further embodiment of the invention, specifically an apparatus 10e generally comprising an appliance 20 having a helical or spiral spring including coils 22 comprising, for example, a super-elastic material, as described elsewhere herein.

FIGS. 7-11 show various other embodiments of the invention that are generally non-circumferential in structure. Except as expressly described herein, each of the apparatus 10f, 10g, 10h, 10i and 10j, shown in FIGS. 7-11 respectively, is similar to apparatus 10 and is structured, unless otherwise noted herein, to be utilized for the treatment of sleep apnea and/or snoring as herein noted.

Figure 7:
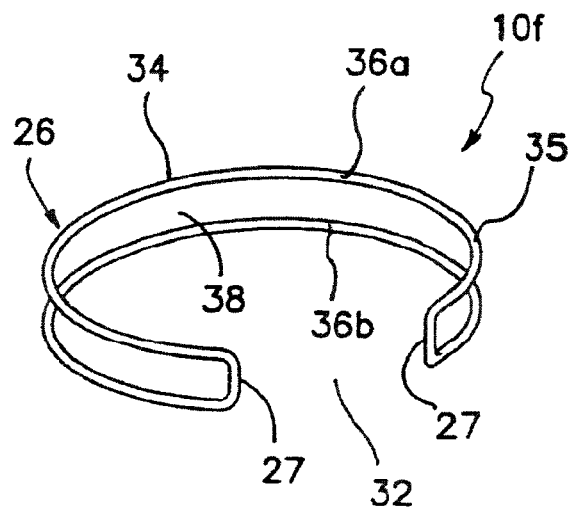

Turning now specifically to FIG. 7, the present invention preferably provides apparatus 10f, comprising an appliance 26 that is non-circumferential in structure. In other words, apparatus 10f, unlike apparatus 10a-10e, includes spaced apart end portions 27 defining a gap 32, and a closed portion 34. The end portions 27 are preferably rounded as shown.

More specifically, the appliance 26 may be described as comprising a substantially C-shaped member 35 defining a pair of resilient, flexible wire struts 36a and 36b connected at the end portions 27. The struts 36a and 36b may have any suitable transverse cross-section, for example, a circular, oval, rounded, flattened or the like transverse cross-section. In this particular embodiment of the invention, the member 35 comprises a wire or ribbon that forms a continuous loop as shown, defining an open interior space 38.

Still referring to FIG. 7, the appliance 26 is structured to be positioned within the oropharyngeal region with the end portions 27 bearing against and providing an opening force against the lateral walls of the oropharyngeal region. It is contemplated that the apparatus 10f may be alternatively positioned such that the appliance 34 rests substantially within or entirely within the valecullar space and presses against the base of the tongue along closed portion 34.

Upon contraction of the oropharyngeal region, for example, during swallowing, the end portions 27 will be temporarily forced toward one another by the muscles in the oropharyngeal region, and may or may not overlap or contact one another. The flexibility and relative spacing of the struts 36a and 36b allow the appliance 34 to contract and expand in vertical and horizontal directions as necessary, for example in conjunction with peristalsis of the pharyngeal walls upon swallowing.

Preferably, each of the embodiments of the present invention is comprised of highly elastic, resilient, biocompatible materials. In particular, each of the non-circumferential apparatus in accordance with the present invention preferably comprises a metallic material, and/or a super-elastic material, more preferably, a nickel titanium (NiTi) alloy, such as the alloy known as Nitinol.

Intrinsically, the present appliances made of such metals such as Nitinol provide reinforcement and/or support to the pharynx without altering, or at least without substantially altering, the pharyngeal tissues and without or interfering with the physiological structure of the pharyngeal tissue itself. Advantageously, the use of such metallic materials provides enhanced control of the degree of stiffening and/or reinforcement of the pharyngeal region because the intrinsic properties of the appliance itself, for example the dimensions and resiliency thereof, are relied upon to treat the patient's condition. This is in contrast to treating a patient with a device intended to induce or promote one or more tissue reactions, for example, fibrosis, other scarring of tissues and the like reactions, near the device to effect stiffening or other changes in the pharyngeal region.

For general background purposes, a description of the benefits of Nitinol for use in the present invention follows. Additional details of this alloy can be obtained from readily available sources and/or will be known to those of skill in the art.

Nickel titanium (also known as Nitinol) is in the class of materials known as shape memory alloys. A thermoelastic martensitic phase transformation in the material is responsible for its extraordinary properties. These properties include the shape memory effect, super-elasticity, and high damping capability.

Nitinol has the ability to absorb large amounts of strain energy and release it as the applied strain is removed. Nitinol also has excellent torqueability and kink resistance, which is an important feature of the apparatus of the present invention due to the dynamic nature of the oropharyngeal and hypopharyngeal regions. Advantageously, super-elastic Nitinol alloys provide a substantially constant force over a large strain range.

The present apparatus more preferably comprise a Nitinol material, more preferably with a ratio of the two constituents, nickel and titanium, at about 50 atomic percent each (about 55 percent by weight of nickel).

The properties of Nitinol can be modified by changes in alloy composition, mechanical working, and heat treatment, as known to those of ordinary skill in the art. The specific alloy used in the apparatus of the present invention is selected mainly for its super-elastic effect rather than its shape memory effect.

Super-elastic Nitinol alloys preferably are used in the apparatus of the present invention to take advantage of a stress-induced martensitic transformation in order to achieve extreme amounts of flexibility and kink resistance. It is known that an alloy of nickel and titanium can behave super-elastically if its Active $A_f$ temperature is just below the use temperature. For example, alloys which are intended to be super-elastic at room temperature are generally produced with their Active $A_f$ temperatures just below room temperature in the range of about 0 to about 20° C. A super-elastic material will not be super-elastic at all temperatures, but will exhibit good super-elastic properties in a temperature window extending from the Active $A_f$ temperature up to a temperature which is about 50° C. above Active $A_f$. Therefore, a material with an Active $A_f$ of about 15° C. will exhibit good super-elasticity up to about 65° C., which means that the material will exhibit good super-elasticity at both room temperature and body temperature (37° C.).

Nitinol is the more preferred material for the apparatus of the present invention also due to its excellent biocompatibility, very high corrosion resistance, and excellent cytocompatibility. In addition, the nickel in nickel/titanium alloy is chemically joined to the titanium in a strong intermetallic bond, so the risk of reaction, even in patients with nickel sensitivity, is extremely low. Additional details on nickel titanium alloys are known to those of ordinary skill in the art and are provided, for example, in Jervis, U.S. Pat. No. 6,306,141, which is incorporated herein in its entirety by this specific reference.

FIGS. 8-10 show alternative embodiments of the invention similar to the embodiment shown in FIG. 7 in that the appliance is non-circumferential as defined elsewhere herein.

More specifically, referring to FIG. 8, an apparatus 10g in accordance with the invention is shown that generally comprises a cuff-shaped appliance 50. Like appliance 26, appliance 50 includes spaced apart end portions 27g defining a gap 32g, and closed portion 34g. A substantial distinction between apparatus 10g and apparatus 10f is that apparatus 10g comprises relatively wide, opposing outer peripheral portions 56a and 56b, that define flattened bands, rather than struts 36a and 36b. The outer peripheral portions 56a and 56b define an open interior space 58. Relative to apparatus 10f, this particular design generally allows greater surface contact with oropharyngeal tissues as well as greater hoop strength or opening pressure.

FIG. 9 shows an apparatus 10h of the invention comprising a cuff-shaped appliance 60 similar to appliance 50 for accommodating a patient with different needs, for example, a patient having a longer, more narrow oropharyngeal region. Appliance 60 includes spaced apart end portions 27h defining a gap 32h and closed portion 34h.

FIG. 10 shows another apparatus 10i in accordance with the invention, the apparatus 10i being similar to the embodiment shown in FIG. 8. A significant distinction between apparatus 10i and apparatus 10g is that the apparatus 10i comprises a substantially mesh structure for providing increased flexibility and/or to facilitate tissue ingrowth to restrict or prevent migration of the apparatus 10i. For example, the appliance 64 comprises an outer peripheral portion 66 made of a woven mesh wire for example, defining an interior space 68.

FIG. 11 shows yet another apparatus 10j in accordance with the present invention, comprising a non-circumferential cuff-shaped appliance 82 having spaced apart end portions 27j defining a gap 32j. A significant distinction between apparatus 10j and apparatus 10g is that appliance 82 does not include interior space 58, but is instead substantially solid as shown. In addition, appliance 82 preferably includes one or more through apertures 87 for facilitating tissue ingrowth.

FIGS. 12-21 show various embodiments of the invention that are generally planar when in a resting or non-deployed state, for example, when the apparatus is located outside of the oropharyngeal region of a patient in a rest position. Except as expressly described herein, each of the apparatus 10k, 10m, 10n, 10p and 10q, 10s, 10t, 10u, 10v and 10w shown in FIGS. 12-21 respectively, is similar to apparatus 10 and is structured, unless otherwise noted herein, to be utilized for the treatment of sleep apnea and/or snoring as herein noted.

Figure 12:
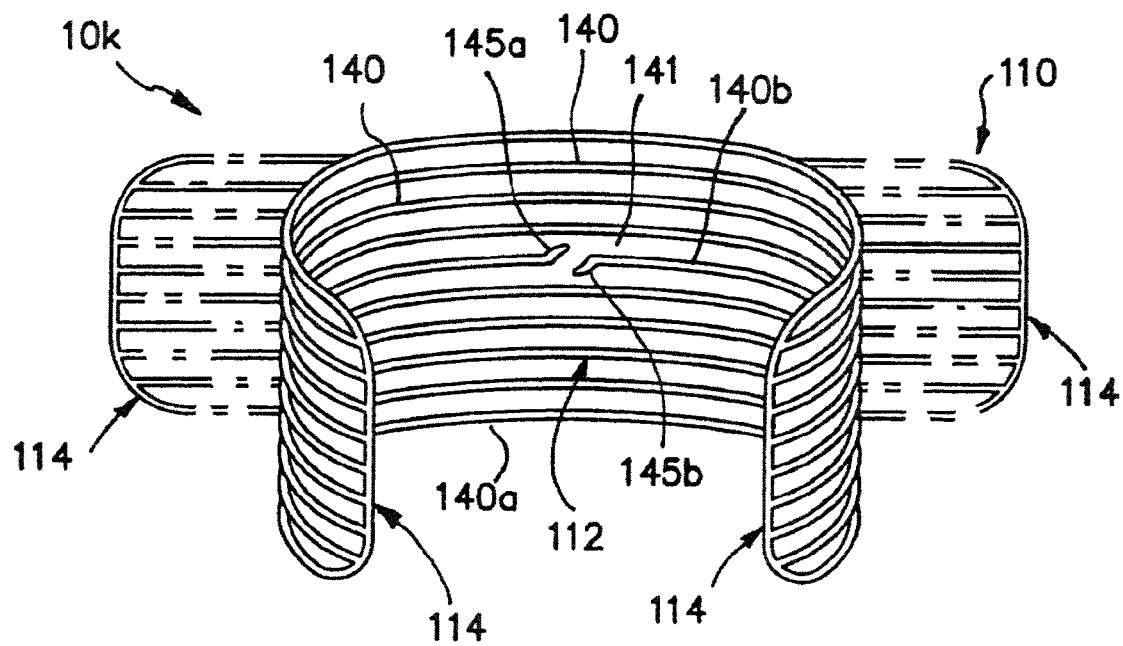
FIG. 12 shows a perspective view of an alternate embodiment of the invention that comprises a flat flexible member including spaced apart struts extending between rounded end portions.

Turning now to FIG. 12, apparatus 10k, in accordance with the present invention, generally comprises an appliance 110 having a flat, or substantially planar configuration (represented by phantom lines) that is flexible to achieve an arched, or curved configuration (shown in solid line). Like the embodiments of the invention shown in FIGS. 7-11, the apparatus 10k defines a non-circumferential configuration when in the deployed state.

More particularly, the appliance 110 comprises a body portion 112 and end portions 114 spaced apart by the body portion 112. The appliance 110 may be in any suitable form, such as, for example, a substantially rectangular (shown in FIG. 12), a substantially circular form, a substantially oblong form, a substantially oval form or a substantially elliptical form or the like configuration. When located in the oropharyngeal region, the appliance 110 is structured to exert a sufficient force, more preferably a sufficient substantially constant radial force, on the oropharyngeal region, particularly against the lateral walls of the oropharyngeal region, to maintain or cause the airway passing through the region to be patent, so that it is substantially open or unobstructed.

The appliance 110 is structured to take on a deployed configuration when located within the oropharyngeal region such that the end portions 114 are spaced apart from each other by other than the body portion 112. For example, the end portions 114 may be spaced apart by the epiglottis or a portion of the anterior or posterior wall of the oropharyngeal region. The apparatus 110 is structured to be sufficiently resilient and flexible to allow for normal dynamic movement or motion of the oropharyngeal region with little or no loss in desirable properties, such as hoop strength and the like, over an extended period of wear.

Advantageously, the apparatus 10k may be formed entirely from a unitary flat sheet of material that is laser cut into the desired configuration. Using a flat elastic or super-elastic sheet of material or a sheet pre-curved to a diameter larger than that of the oropharyngeal region of the human or animal, the apparatus 10k, once implanted into the oropharyngeal region, applies substantially continuous opening pressure to the oropharyngeal walls, for example, the lateral walls of the oropharyngeal region.

Appliance 110 may have a length of between about 50 mm and about 90 mm in the substantially flat configuration, and a height of between about 15 mm and about 25 mm. The dimensions of appliance 110 are selected based on individual patient need. The appliance is designed such that the effective non-constrained diameter of the appliance, when deployed, is greater than about 32 mm.

Appliance 110 comprises a plurality of flexible wire or ribbon struts 140, which preferably extend between the radiused end portions 114 extending along a substantial portion of the length of the appliance 110. For example, the appliance 110 may comprise between about 2 and about 50 struts or more, and preferably between about 6 and about 20 struts, such as about 10 struts.

In the embodiment shown in FIG. 12, each of the struts 140 has a thickness of about 0.005 inch and a width of about 0.010 inch. This design has been found to provide the required flexibility and resiliency in at least three dimensions or directions of motion, and preferably, in addition, twisting motion, without exhibiting significant fatigue over an extended period of wear/time in service requiring dynamic movement, such as in the oropharyngeal region.

The number, thickness, and width of the struts 140 may be varied to produce a desired opening pressure (e.g., hoop strength) on the base of the tongue or to reduce or increase the surface area of the struts 140 which are in contact with the oropharyngeal walls. This design also allows improved vertical collapse/deformation of the oropharyngeal region, for example, allowing peristalsis type movement during swallowing.

When provided in an oropharyngeal region of a patient for the treatment of sleep apnea and/or snoring, the appliance 110 is curved with a convex surface pressing against the tissues to be supported, particularly the lateral walls of the oropharyngeal region and/or the base of the tongue.

The appliance 110 is structured to be self-expanding with a controlled length during such expansion. This can be achieved by suitable selection of super-elastic materials, preferably Nitinol, and appropriate selection of strut length and other dimensions. The appliance 110 also is preferably structured to have a relatively atraumatic nature of all surfaces thereof and of the curved end portions. In addition, the appliance 110 is structured to exhibit the ability to be delivered in a minimal diameter access manner by rolling the appliance 110 onto itself within a catheter, inserter tube and the like.

The appliance 110 may be tailored to be effective in a variety of patients and in a variety of different body regions that would benefit from the consistent support provided by such an appliance. For example, the size and structure of the appliance can be selected to accommodate a specific need. The amount of force provided by the appliance can be modified by appropriate selection of the number of struts, width and/or thickness of struts, and/or surface area covered by the struts and/or the like factors. Generally, as the struts become thinner and take up less surface area, the appliance 110 will become more compliant and will move and flex with less radial force exerted thereby and will flex to a greater extent without permanent deformation. It is noted that a portion of appliance 110 may be modified such that it will function to anchor or secure the appliance in place. For example, an outer or peripheral strut 140a may be configured to achieve a "fluted" configuration. In some embodiments, although not shown, one or more of the struts may be shaped as wave forms or s-shapes. In yet other embodiments, although not shown, cushioned end members may be provided on the end portions 114 of the appliance 110 in order to enhance comfort and/or proper fit.

An optional feature of the invention is shown at 141 for facilitating anchoring of the apparatus 10k in the given position. More specifically, at least one of the struts 140b may be configured to form barbed portions 145a and 145b for enhancing secure attachment of the appliance 110 to the posterior wall of the oropharyngeal region. It is also contemplated that other means for securing the apparatus 10k in the given position may be provided, for example, surfaces of the apparatus 10k may be coated with a biologically compatible glue or adhesive.

Figure 13:
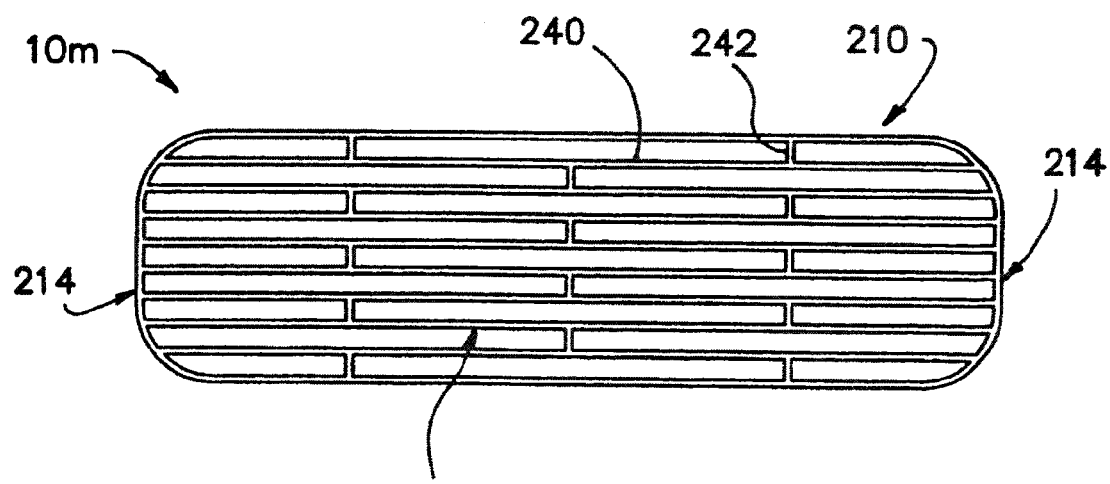
FIGS. 13-16 show, in plan view, other alternate embodiments of the invention similar to the embodiment shown in FIG. 12.

FIG. 13 shows another apparatus 10m including appliance 210 for treating sleep apnea and/or snoring, in accordance with the present invention. Apparatus 10m is similar to apparatus 10k, with an additional feature shown on apparatus 10m being the addition of spacing portions 242, positioned and structured to maintain a spaced apart relationship between adjacent struts 240 when apparatus 10m is in the oropharyngeal region of a patient. Appliance 210 includes end portions 214 and body portion 212.

Figure 14:
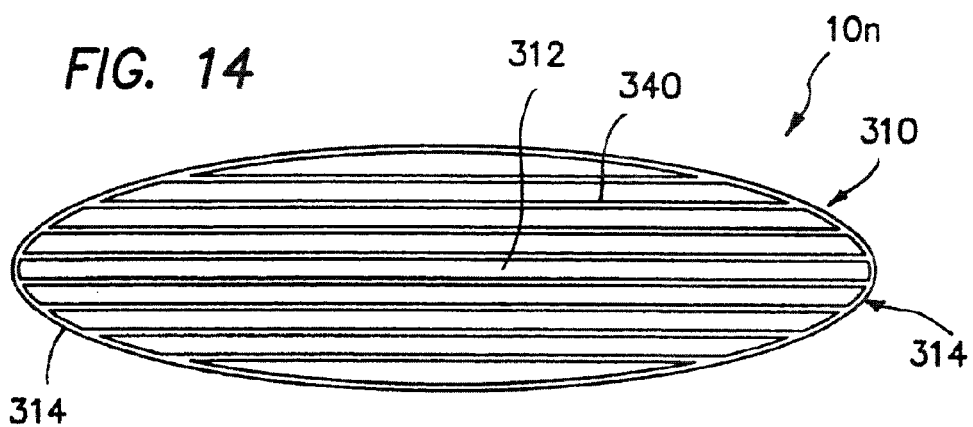
Figure 15:
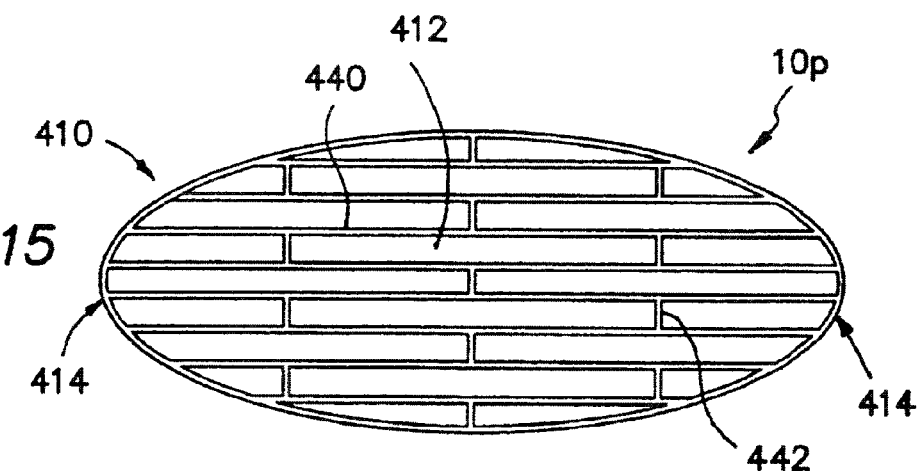

FIGS. 14 and 15 show apparatus 10n and 10p respectively, for treating sleep apnea and/or snoring, in accordance with the present invention. Apparatus 10n and apparatus 10p are similar to apparatus 10k and 10m, with the most significant distinction being that apparatus 10n and 10p are substantially oval or elliptical rather than rectangular in shape. Apparatus 10n generally comprises appliance 310 including rounded end portions 314 joined by body portion 312, and a plurality of spaced apart struts 340. Apparatus 10p generally comprises appliance 410 including rounded end portions 414 joined by body portion 412, and a plurality of spaced apart struts 440 and spacing portions 442.

Figure 16:
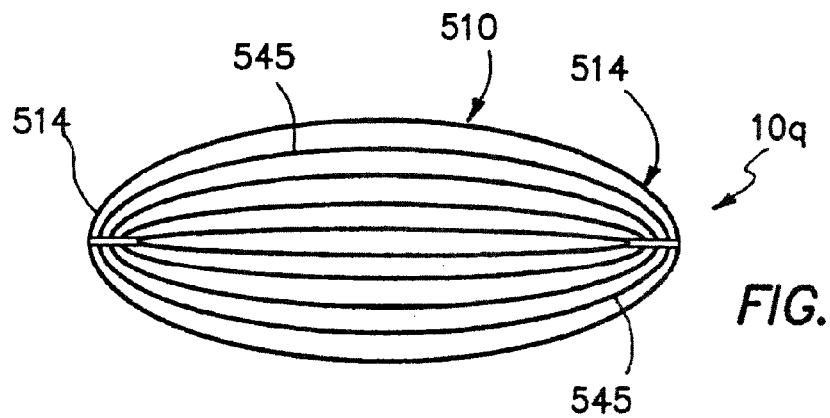

FIG. 16 shows yet another apparatus 10q for treating sleep apnea and/or snoring in accordance with the present invention. As shown, apparatus 10q comprises an appliance 510 having a substantially elliptical shape and including a plurality of bowed or arched struts 545 that converge at end portions 514.

Turning now specifically to FIGS. 17-21, additional alternative embodiments of the present invention are shown. Like the embodiments of the invention shown in FIGS. 12-16, these embodiments are typically planar in structure when at rest and not deployed in the oropharyngeal region of a patient. A significant distinction between the embodiments shown in FIGS. 12-16 and the alternative embodiments shown in FIGS. 17-21, is that the latter embodiments each preferably define a single continuous loop.

Figure 17:
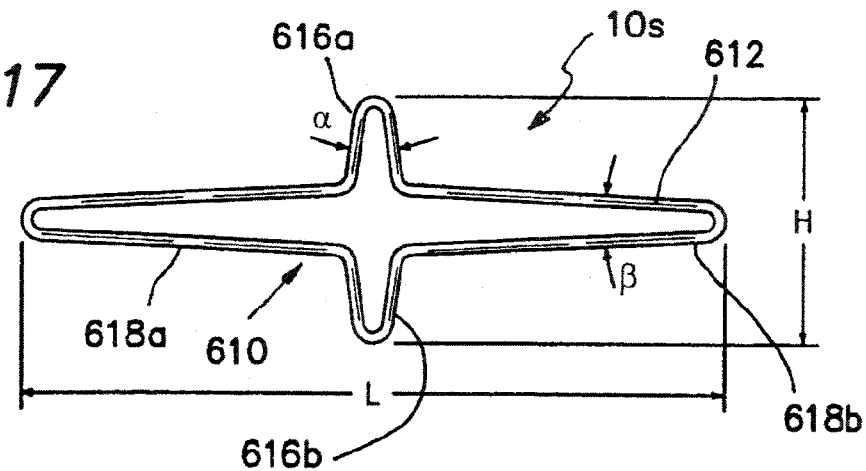
FIGS. 17-21 show, in plan view, various other alternative embodiments of the invention comprising a single loop element.

More specifically, FIG. 17 shows an apparatus 10s for treating sleep apnea and/or snoring in accordance with the present invention, comprising a substantially cross-shaped appliance 610, defined by a single loop element 612. The appliance 610 preferably is cut, more preferably photoetched, from a single sheet of material, preferably a sheet comprising a Nitinol superelastic alloy material, and preferably having a sheet thickness of about 0.01 inch to about 0.1 inch. Element 612 preferably has a substantially uniform width of between about 1 mm to about 5 mm or greater. The appliance 610 preferably has a height H along a vertical axis of about 15 mm to about 25 mm, and a length L along a horizontal axis of about 60 mm to about 90 mm allowing an effective non-constrained diameter of greater than about 32 mm. The cross-shaped appliance 610 preferably is symmetrical about its vertical and horizontal axes. Appliance 610 includes vertical portions 616a and 616b each defining an angle α, and horizontal portions 618a and 618b each defining an angle β.

For purposes of example only, not to be considered limiting the scope of the present invention, vertical portions 616a and 616b define a peak-to-peak measurement (i.e. height H) of about 25 mm, and horizontal portions 618a and 618b define a peak-to-peak measurement (i.e. length L) of about 70 mm. Also for purposes of this specific example only, each of vertical portions 616a and 616b defines an angle α of about 15° and each of horizontal portions 618a and 618b defines an angle β of about 6°.

Appliance 610 is structured to be placed in the oropharyngeal region in a position such that horizontal portions 618a and 618b rest against and provide support to the lateral walls of the oropharyngeal region. The vertical axis of the apparatus 610, generally defined by vertical portions 616a and 616b, are disposed against or adjacent the posterior wall of the oropharyngeal region.

Figure 18:
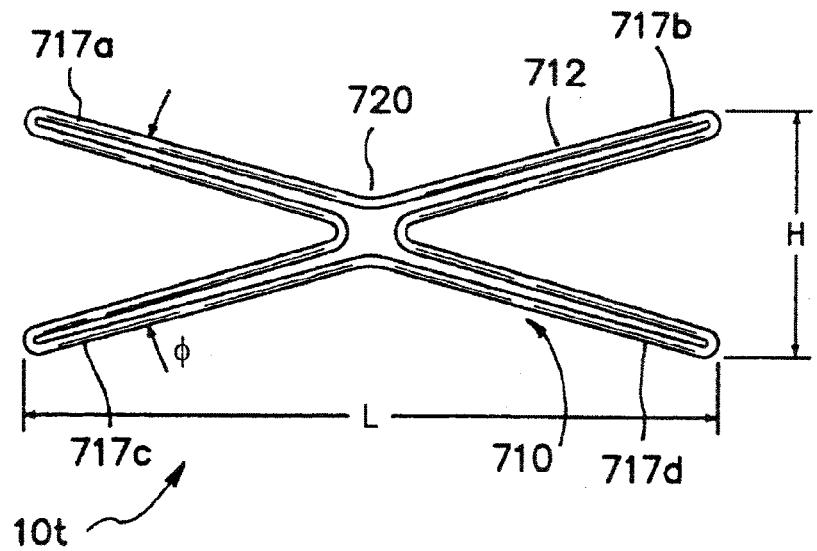

FIG. 18 shows yet another apparatus 10t for treating sleep apnea and/or snoring in accordance with the present invention. Apparatus 10t is similar to apparatus 10s in that it is defined by a single loop element 712 cut from a single sheet of material, for example, a Nitinol alloy. A substantial distinction between apparatus 10s and apparatus 10t is that, rather than comprising a cross-shaped appliance 610, apparatus 10t comprises a substantially X-shaped appliance 710 having a length L and a height H. Appliance 710 includes multiple leg portions 717a, 717b, 717c and 717d extending from a generally central region 720, wherein paired leg portions 717a and 717c and paired leg portions 717b and 717d, both define an angle ϕ. For purposes of this specific example only, not to be considered limiting the scope of the present invention, appliance 710 has a length L of about 70 mm and a height H of about 25 mm, and angle ϕ is about 36°.

Appliance 710 is structured to be placed in the oropharyngeal region in a position such that leg portions 717a, 717b, 717c and 717d rest against and provide support to the lateral walls of the oropharyngeal region, and the generally central portion 720 is disposed against or adjacent the posterior wall of the oropharyngeal region.

Figure 19:
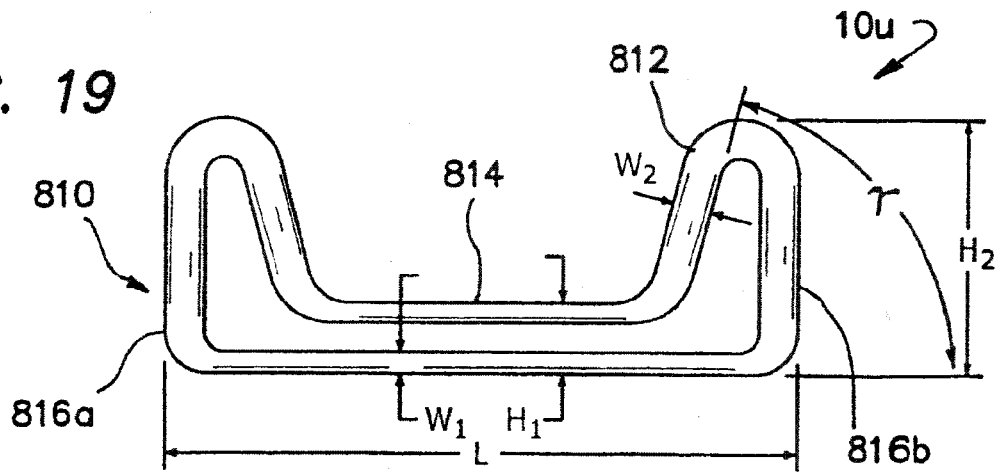

FIG. 19 shows yet another apparatus 10u for treating sleep apnea and/or snoring in accordance with the present invention. Apparatus 10u is similar to apparatus 10s in that it is defined by a single loop element 812 cut from a single sheet of material, for example, a Nitinol alloy. Apparatus 10u comprises an appliance 810 having a relatively narrow, generally central body portion 814 (having height $H_1$) terminating at relatively wide end portions 816a and 816b (having height $H_2$), and a length L. End portions 816a and 816b preferably define angle γ as shown.

For purposes of this specific example only, not to be considered limiting the scope of the present invention, appliance 810 has a length L of about 85 mm, a height $H_1$ of about 10 mm, a height $H_2$ of about 35 mm, and an angle γ of about 75°. Element 812 has a width $W_1$ at generally central portion 814 and a width $W_2$ of about 5 mm at end portions 816a and 816b.

Appliance 810 is structured to be placed in the oropharyngeal region in a position such that end portions 816a and 816b rest against and provide support to the lateral walls of the oropharyngeal region, and the generally central body portion 814 is disposed against or adjacent the posterior wall of the oropharyngeal region.

Figure 20:
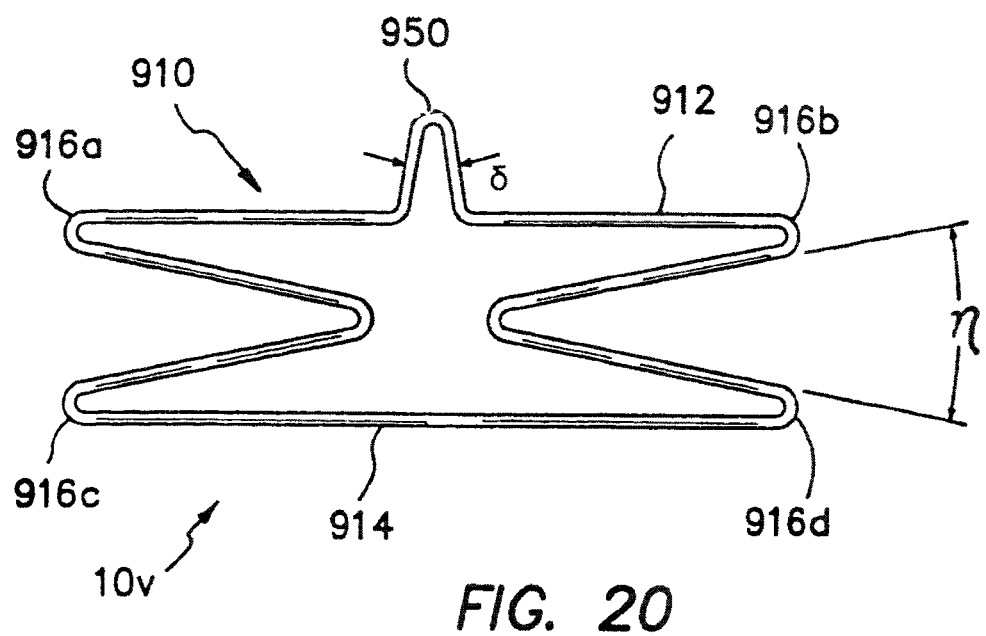

FIG. 20 shows yet another apparatus 10v for treating sleep apnea and/or snoring in accordance with the present invention. Apparatus 10v comprises an appliance 910 comprising loop element 912, and including a generally central body portion 914, and multiple end portions 916a, 916b, 916c and 916d. As shown adjacent end portions define an angle η. Appliance 910 further includes a vertical portion 950 that defines an angle δ.

Appliance 910 is structured to be placed in the oropharyngeal region in a position such that multiple end portions 916a, 916b, 916c and 916d rest against and provide support to the lateral walls of the oropharyngeal region, and the generally central body portion 914 is disposed against or adjacent the posterior wall of the oropharyngeal region.

Figure 21:
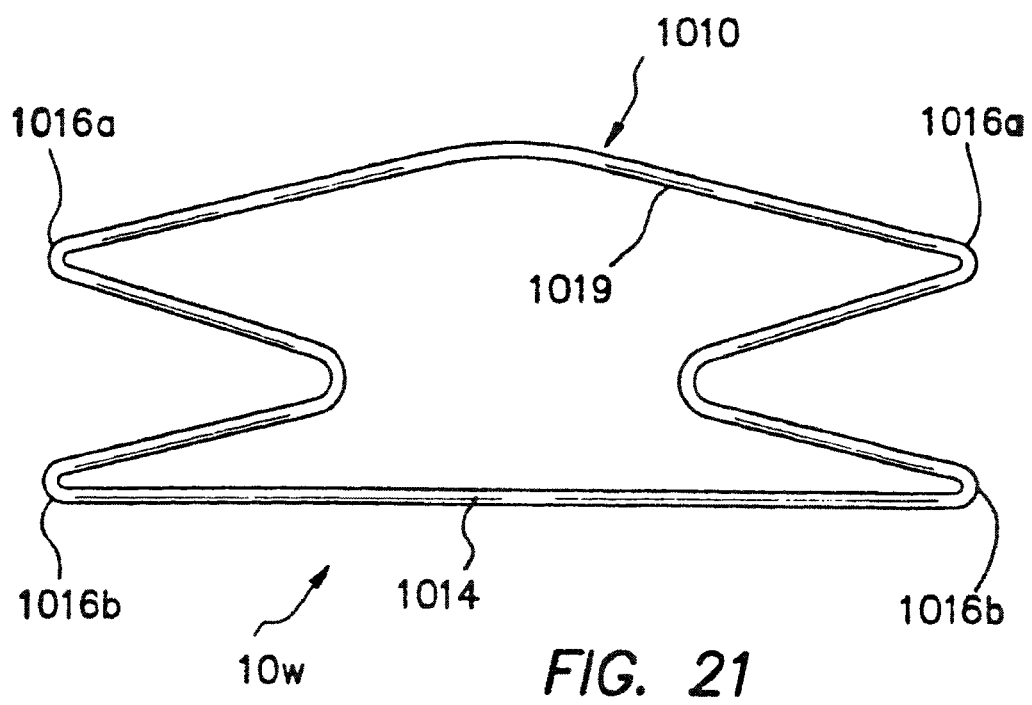

FIG. 21 shows yet another apparatus 10w for treating sleep apnea and/or snoring in accordance with the present invention. Apparatus 10w comprises an appliance 1010 that is somewhat similar to appliance 910 in that appliance 1010 includes a generally central body portion 1014 and multiple end portions 1016a, 1016b, 1016c and 1016d. Appliance 1010 has somewhat different proportions, including a relatively wide upper central portion 1019 that is configured to provide enhanced tissue support to portions of the posterior wall of the oropharyngeal region, relative to tissue support provided by appliance 910.

Figure 22:
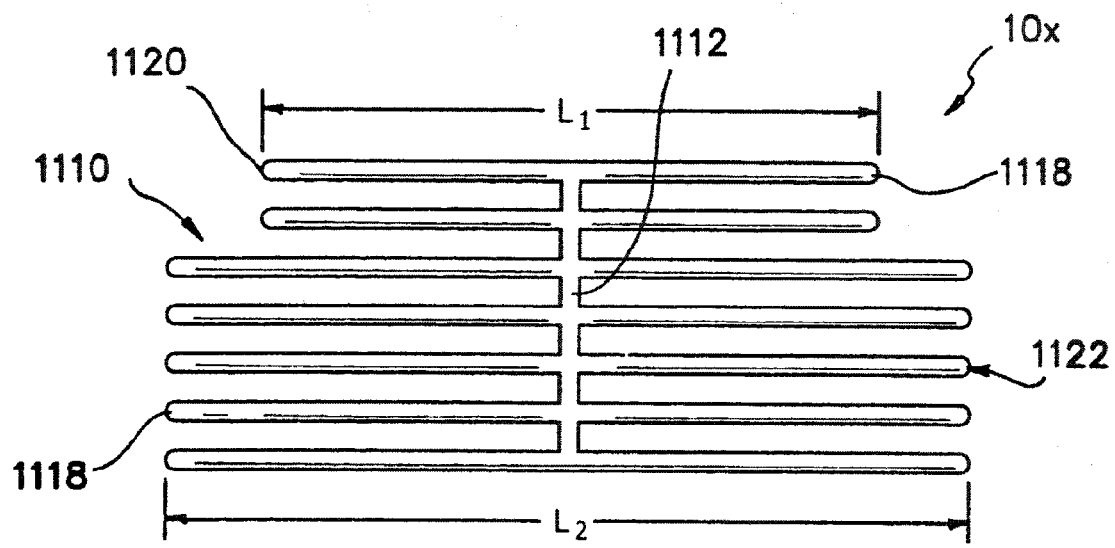
FIGS. 22-23 show, in plan view, yet other embodiments of the invention.
Figure 23:
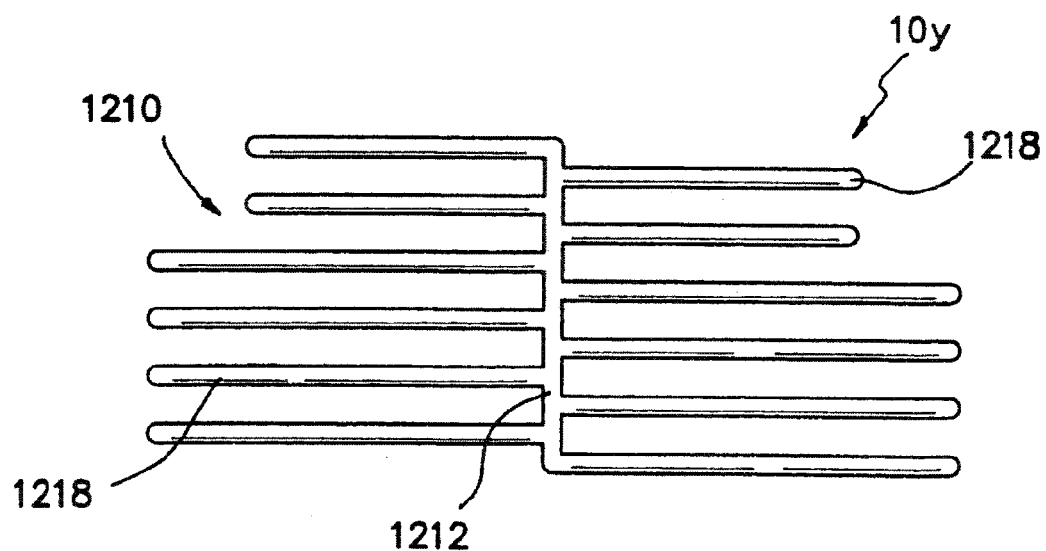

FIGS. 22-23 show other embodiments of the invention for treating sleep apnea and/or snoring. Like the embodiments of the invention shown in FIGS. 12-22, these embodiments are typically planar in structure when at rest and not deployed in the oropharyngeal region of a patient.

FIG. 22 shows an apparatus 10x in accordance with the invention comprising a substantially symmetrical appliance 1110 including a substantially linear body portion 1112 and a plurality of struts 1118 extending from the body portion 1112, for providing support to the oropharyngeal tissues. The number and length of struts 1118 preferably are selected based on a particular patient need. For purposes of example only, appliance 1110 may have an upper portion 1120 having about two pairs of struts 1118 defining a tip to tip length $L_1$ of about 62 mm, and a lower portion 1122 having about five pairs of struts 1118 defining a tip to tip length $L_2$ of about 82 mm.

FIG. 23 shows an apparatus 10y in accordance with the invention that is similar to apparatus 10x. The most significant distinction is that apparatus 10y comprises an appliance 1210 that includes a body portion 1212 and struts 1218 that are offset from one another along body portion 1212.

Figure 24:
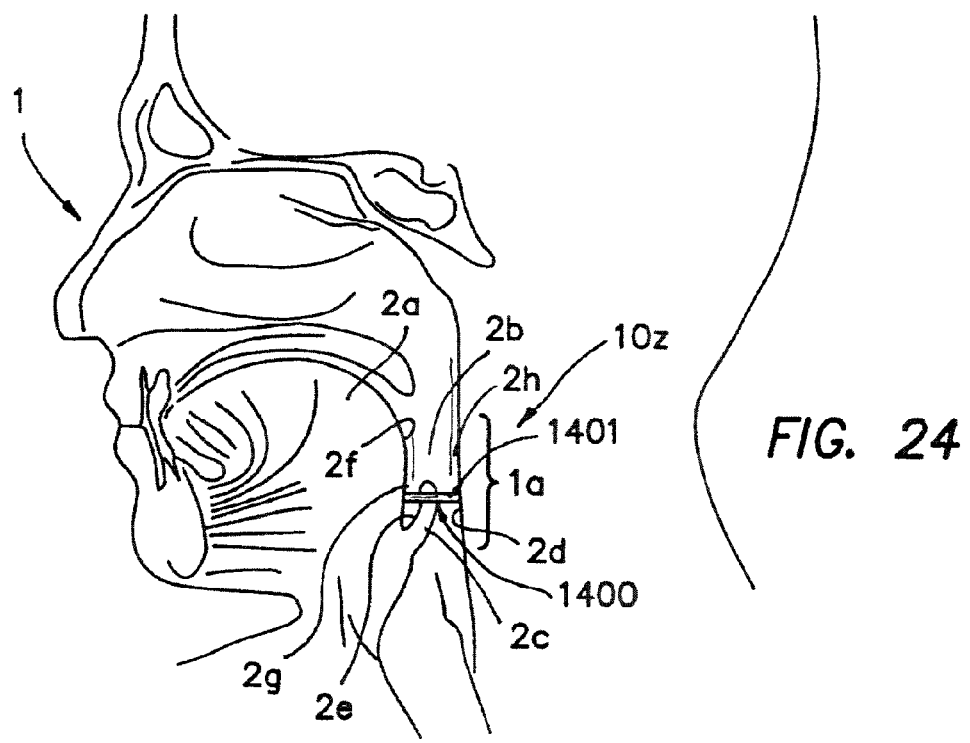
FIG. 24 shows a side view of a preferred embodiment of the invention in which the apparatus comprises an elongated element structured to be at least partially submucosally implanted in the pharyngeal region of a patient.

Turning now to FIG. 24, a preferred embodiment of the invention is shown, generally at 10z. Apparatus 10z is similar to apparatus 10a through apparatus 10x in that apparatus 10z is structured to be effective in maintaining patency of the airway of a patient 1, for example, the oropharyngeal region 1a of a patient. However, apparatus 10z is specifically structured to be at least partially, and in some cases substantially entirely submucosally, implantable into the pharyngeal region, for example the oropharyngeal region, of the patient.

Figure 25:
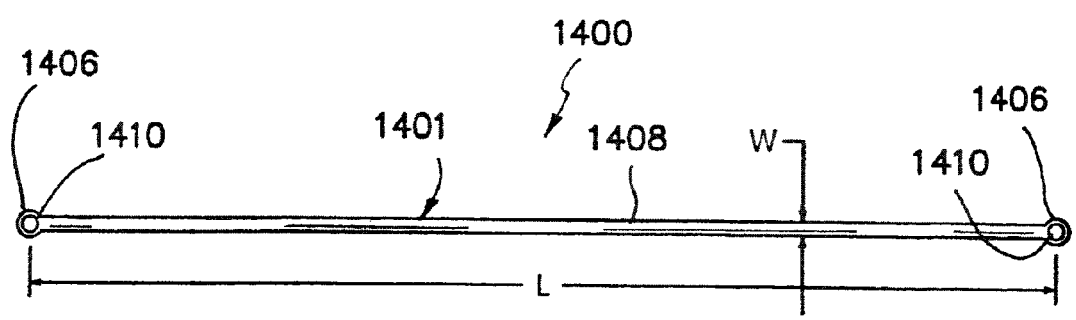
FIG. 25 shows a plan view of the embodiment of the invention shown in FIG. 24.

Apparatus 10z, more clearly shown in FIG. 25, preferably comprises a single elongated element 1401 having end portions, for example, rounded end portions 1406 and a body portion 1408 extending or connected therebetween.

Figure 25A:
FIGS. 25a and 25b show cross-sectional views of alternative cross-sectional shapes of the embodiment of the invention shown in FIG. 25.
Figure 25B:
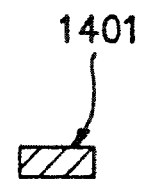

As shown, end portions 1406 are preferably structured to facilitate implantation, for example, surgical implantation, of the element 1401. For example, end portions 1406 may include appropriately sized apertures 1410 for receiving suturing thread. The element 1401 may have a rounded cross-section such as shown in FIG. 25a, or a polygonal cross section, for example a rectangular cross section, such as shown in FIG. 25b.

Referring still to FIG. 25, element 1401 preferably has a length L of between about 50 mm and about 70 mm and a width W of between about 2 mm or less and about 6 mm. Dimensions of the appliance 1400 may be at least in part based upon, for example, the size or diameter of the patient's pharyngeal region and the specific portion of the pharyngeal region to be supported by the apparatus 10z. A typical area of support as mentioned elsewhere herein, is the area encompassing, at least, a portion of one or more of the lateral walls of the oropharyngeal region.

Appliance 1400 may comprise a metallic material such as Nitinol, or a non-metallic material such as Dacron®, or any suitable, flexible, elastic, resilient biocompatible material as discussed elsewhere herein.

Advantageously, the element 1401 is designed to be surgically implantable in the pharyngeal region, at least partially circumscribing the region, and at least partially, preferably substantially entirely, beneath the mucosal layer thereof. The appliance 1400 may also be at least partially sutured to the pharyngeal tissues, for example, at end portions 1401a of the element 1401, and/or secured to the oropharyngeal tissues by means of a biocompatible adhesive.

Figure 26:
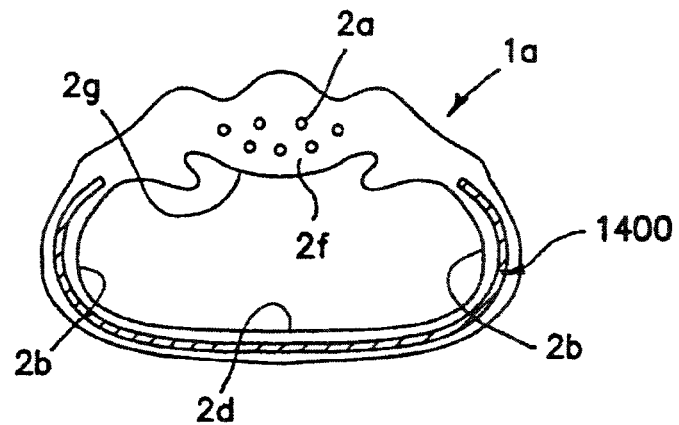
FIGS. 26-28 each show a simplified view of the oropharyngeal region having various apparatus of the invention submucosally implanted therein.

Turning now to FIG. 26, appliance 1400 is shown sized to be placed at least partially circumscribing an interior hollow passage (representing a cross-section of the airway of the patient) defining the pharyngeal region. This view (as well as views shown in FIG. 27 and FIG. 28) is a simplified representation of a cross-section of the oropharyngeal region 1a, with posterior wall 2d and anterior wall 2g, (which includes the base 2f of the tongue 2a) and opposing right and left lateral walls 2b. This placement of appliance 1400 is effective in providing support to the lateral walls 2b of the oropharyngeal region 1a. The appliance 1400 is shown substantially entirely submucosally implanted.

Figure 27:
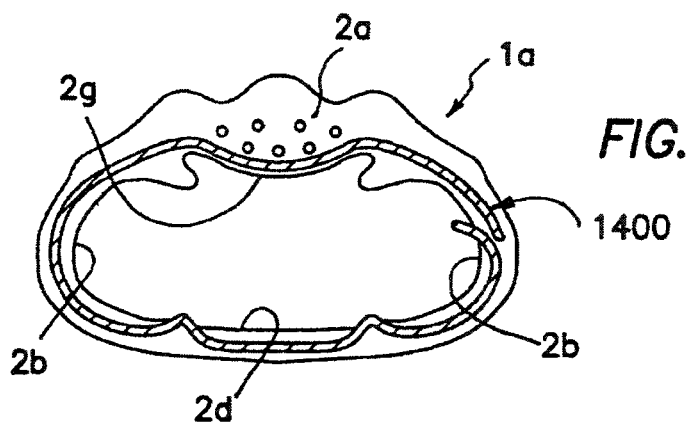

Turning now to FIG. 27, appliance 1400 is shown sized to be placed circumscribing, at least one full circumference of, the interior hollow space defined by the pharyngeal region. In this case, the appliance 1400 is sized to traverse the base 2f of the tongue 2a, for example, beneath the mucosal tissue thereof. The appliance 1400 is shown partially submucosally implanted.

Figure 24A:
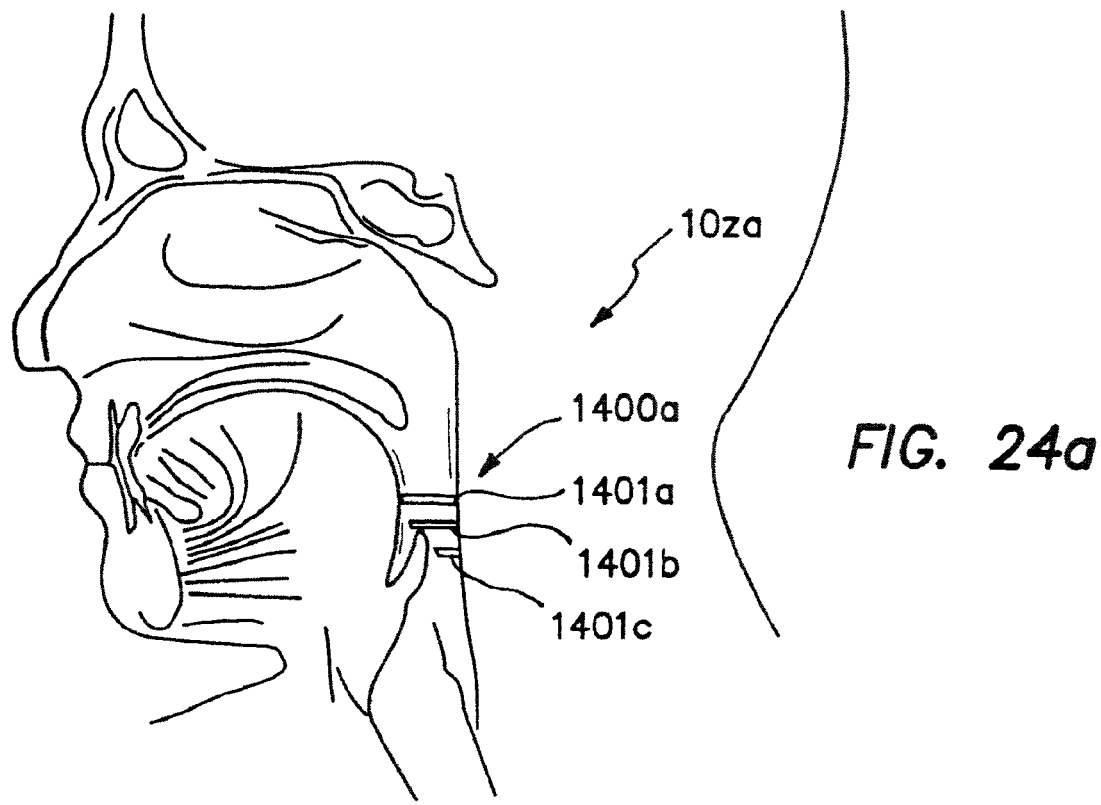
FIG. 24a shows an alternative cross section of an embodiment of the invention similar to the embodiment shown in FIG. 24, comprising multiple, spaced apart elongated elements at least partially submucosally implanted within the oropharyngeal region of a patient.

FIG. 24a shows another apparatus, generally at 10za, in accordance with the present invention. Apparatus 10za is substantially similar to apparatus 10z, except that apparatus 10za comprises an appliance 1400a including a plurality of elongated, spaced apart elements, for example at least two, or three or even more spaced apart elements 1401a, 1401b, and 1401c, depending upon the specific needs of a particular patient. Except as indicated elsewhere herein, it is to be appreciated that elements 1401a, 1401b and 1401c are structured to be placed, for example, at least partially submucosally, implanted in a manner as described hereinabove with respect to element 1401.

Each element 1401a, 1401b, and 1401c may be substantially, entirely independent, or unitary, in structure with respect to each other element 1401a, 1401b, and 1401c. Alternatively, the multiple elements 1401a, 1401b, and 1401c may be secured to each other by suitable means, for example, suturing, wire, ribbon or the like, for substantially maintaining the spaced apart relationship between the elements 1401a, 1401b, 1401c when the elements 1401a, 1401b, 1401c are positioned within and secured to the pharyngeal region.

In a related embodiment of the invention, a method is provided for maintaining patency of a pharyngeal region. Particularly, the method may comprise the step of at least partially submucosally placing at least one elongated element within the pharyngeal region, for example the oropharyngeal region in one or more strategic locations, wherein the placement thereof will cause the region to be stiffened or strengthened against collapse during natural sleep.

Figure 28:
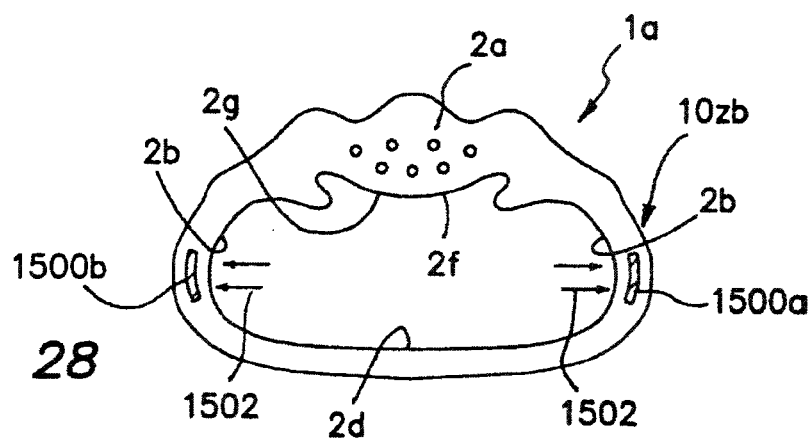

To illustrate another optional feature of the present invention, FIG. 28 shows a simplified view of the oropharyngeal region 1a of a patient, having apparatus 10zb in accordance with an embodiment of the invention, submucosally implanted therein. FIG. 28 may represent an apparatus 10zb comprising one or more magnetic components 1500a and 1500b, structured and designed to be effective to provide a magnetic field useful for providing gentle, substantially constant and continuous resistance against collapse of the pharyngeal walls, particularly the lateral walls 2b of the oropharyngeal region 1a, for example during natural sleep, while allowing substantially normal functioning of the pharyngeal region, for example during swallowing.

In the example shown, the two magnetic components 1500a, 1500b are strategically placed within the oropharyngeal region 1a such that like magnetic poles (i.e. repellant magnetic poles) are positioned substantially facing one another to create a magnetically repellant force therebetween (indicated in simplified form by arrows 1502). The repellant force caused by the strategically placed magnetic components 1500a and 1500b is effective for providing an opening force within the oropharyngeal region, thereby maintaining patency of the region during natural sleep while still allowing constriction of the region during swallowing.

FIG. 28 is also provided to illustrate an embodiment of the invention in which the apparatus 10zb comprises elongated, non-magnetic, metallic, non-fibrosis inducing elements 1500a and 1500b, shown in cross sectional view, and being elongated, that is extending horizontally within the pharyngeal wall with the patient in the supine position, that is, substantially parallel to the longitudinal axis defined by the pharyngeal walls. In this embodiment, the elements 1500a and 1500b are implanted submucosally parallel to a longitudinal axis defined by the patient's pharynx. Although only two such elements 1500a and 1500b are shown, it is to be appreciated that only one such element, or more than two such elements, may be implanted into the patient depending on individual patient needs. Also, the size, dimensions and shape of such element or elements may be varied, for example depending on the needs of the patient being treated.

Figure 29:
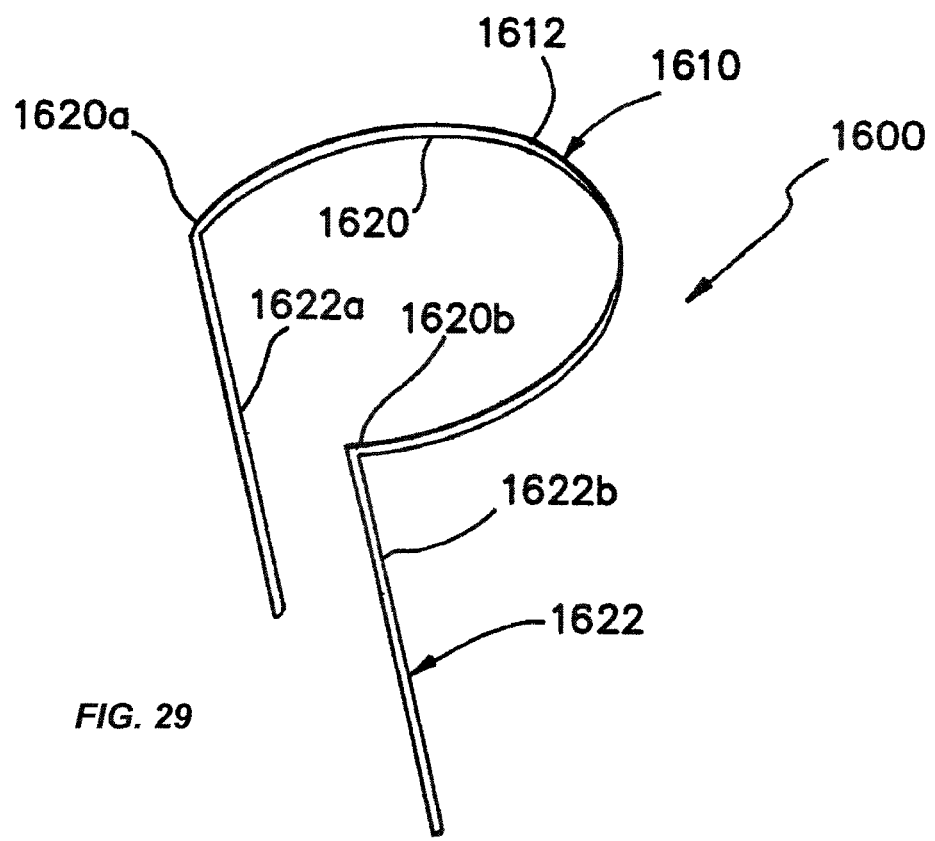
FIG. 29 shows a simplified perspective view of another embodiment of the invention including an element having a transverse portion and two substantially longitudinal portions depending from, and spaced apart by, the transverse portion.

FIG. 29 shows a simplified perspective view of another apparatus 1600 in accordance with the present invention. Apparatus 1600 comprises an appliance 1610 including an element 1612 having a transverse portion or component 1620 with spaced apart ends 1620a and 1620b, and two substantially longitudinal portions or members 1622a and 1622b depending from, and spaced apart by, the transverse portion 1620. Apparatus 1600 is a single, unitary structure made of metal, e.g. Nitinol and the like, or other material so as to inhibit or even substantially eliminate fibrosis or a fibrotic response or reaction from the pharyngeal tissues when the apparatus is placed in the pharyngeal region.

Preferably, each of the two longitudinal portions 1622a and 1622b depends from a corresponding spaced apart end 1620a and 1620b, respectively, of the transverse portion 1620, as shown in FIG. 29.

Advantageously, the transverse portion or component 1620 is sized and structured to be situated along the posterior wall, and possibly at least a portion of the lateral walls, of the oropharyngeal region, to provide a radial force, or an opening force to the walls of the pharyngeal region. The transverse portion 1620 may be secured to the walls of the oropharyngeal region by any suitable means, including one of the many means described elsewhere herein with respect to other embodiments of the present invention.

In one aspect of the invention, the appliance 1610 is surgically implanted into the oropharyngeal region such that the transverse portion 1620 is at least partially submucosally implanted along the posterior wall of the oropharynx, and the longitudinal portions 1622a and 1622b are implanted in substantial alignment with, for example, substantially parallel to, the longitudinal axis of the pharynx or pharyngeal region, for example, within opposing lateral walls of the oropharynx. Preferably, the longitudinal portions or members 1622a and 1622b are substantially entirely submucosally implanted within the pharyngeal region.

FIG. 29A shows a simplified perspective view of another apparatus 1700 of the invention substantially similar to the apparatus 1600 shown in FIG. 29. Unless otherwise expressly specified, apparatus 1700 is substantially identical to apparatus 1600, with like elements indicated by like reference numerals increased by 100. Apparatus 1700 is placed in the pharyngeal region in substantially the same way that apparatus 1600 is so placed.

Apparatus 1700 comprises appliance 1710 having a sloping, for example but not limited to, a downwardly sloping, transverse portion 1720 and two longitudinal portions 1722a and 1722b depending therefrom. In other words, whereas appliance 1610 defines a substantially 90 degree angle between the transverse portion 1620 and the longitudinal portions 1622a and 1622b, the appliance 1710 defines an acute, or alternatively an obtuse (not shown), angle between the transverse portion 1720 and the longitudinal portions 1722a and 1722b.

In other related aspects of the invention, the appliance may have a transverse portion that defines a first angle with one of the longitudinal portions 1722a and 1722b and a second, different angle with the other one of the longitudinal portions 1722a and 1722b.

It is to be appreciated that the desired configuration of the apparatus 1600 or 1700, in many cases, will depend at least in part on the needs of the individual patient being treated.

The transverse portion 1720 of apparatus 1700 provides an additional amount of longitudinal support as well as a radial opening force to the oropharyngeal region. In alternate embodiments of apparatus 1700, the sloping transverse portion 1720 can be used with only one of the longitudinal portions 1722a and 1722b or without either or any of these longitudinal portions. In addition, apparatus including both transverse portions 1620 and 1720, with or without the longitudinal portions 1622a, 1622b, 1722a and/or 1722b, can be employed.

Figure 30:
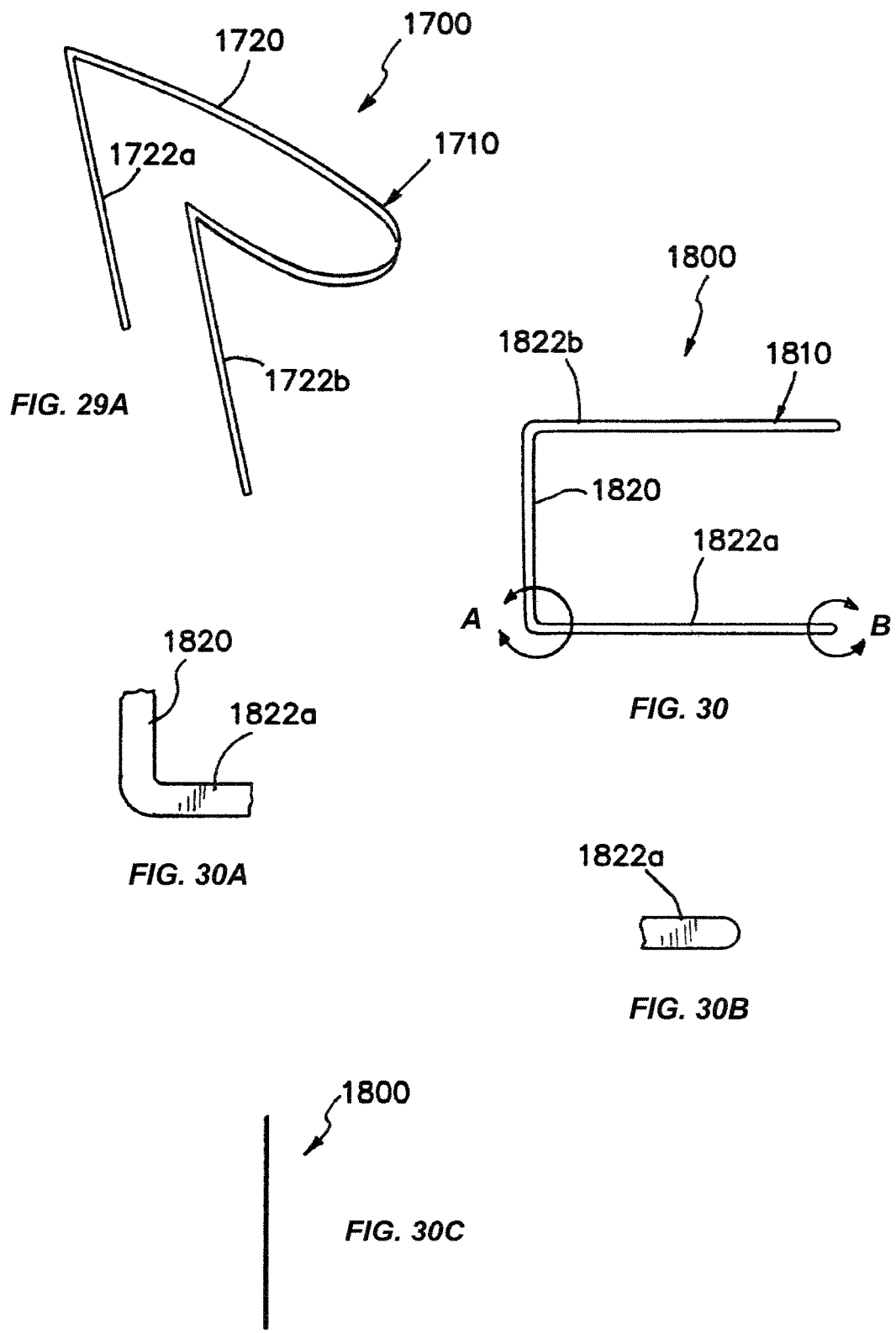
FIG. 30 shows another embodiment of the invention similar to the embodiment shown in FIG. 29, wherein the apparatus includes an appliance having a substantially planar, substantially U-shaped configuration.

FIG. 30 shows another embodiment of the invention substantially similar to the embodiment shown in FIG. 29, wherein the apparatus 1800 comprises an appliance 1810 in a substantially planar, substantially, for example, radiused, squared U-shaped configuration. Like apparatus 1600, apparatus 1800 includes a transverse portion 1820 and longitudinal portions 1822a and 1822b depending therefrom. Unless otherwise expressly specified, apparatus 1800 is structured, is placed in the pharyngeal region, and functions substantially identically to apparatus 1600.

In apparatus 1800, transverse portion 1820 is substantially planar, that is not substantially bow shaped, when the appliance 1810 is at rest outside of the human or animal body.

Like appliance 1610, appliance 1810 is structured to be positioned within the pharyngeal region, for example, the pharyngeal walls, with transverse portion 1820 extending against the posterior oropharyngeal wall and a portion of the lateral walls of the pharyngeal region, and longitudinal portions 1822a and 1822b extending downwardly, preferably submucosally, within the pharyngeal walls, for example, within opposing sidewalls or lateral walls of the oropharyngeal region.

Transverse portion 1820 may have a length of about 0.787 inch (about 20 mm) and longitudinal portions 1822a and

1822*b* may each have a length in a range of about 1.18 inches (about 30 mm) to about 1.97 inches (about 50 mm). Appliance 1810 may have a thickness, for example, a substantially uniform thickness, of about 0.039 inch (about 1.0 mm). The dimensions set forth herein are illustrations and are not intended to limit the present invention. Any of such dimensions may vary widely, for example, by ±about 10%, or ±about 20%, or ±about 40%, or about ±60%, or more, so that the apparatus in accordance with the present invention may meet the treatment needs of a wide variety of individual patients.

FIG. 30A shows a magnified view of a radius of curvature of an outer edge of the radiused angle between longitudinal portion 1822*a* and transverse portion 1820. The radius of curvature may be about 0.040 inch (about 1.0 mm).

FIG. 30B shows a magnified view of a radius of curvature of a distal end of one of the longitudinal portions 1822*a* and 1822*b*. This radius of curvature may be about 0.020 inch (about 0.50 mm).

FIG. 30C shows a side view of the apparatus of FIG. 30 in order to illustrate the relatively thin nature of the apparatus 1800, the apparatus 1800 having a thickness of about 0.008 inch (about 0.20 mm).

When outside the body of the patient, for example, prior to submucosal implantation, the apparatus at rest may have a substantially planar profile as shown in FIG. 30. This configuration is provided in order to simplify and facilitate implantation of the apparatus 1800. Once implanted, the apparatus 1800 conforms to the wall, for example the posterior wall and a portion of the lateral walls, of the pharyngeal region while providing both radial and longitudinal support thereto.

Apparatus 1800 is substantially planar as shown in FIG. 30 after being cut from a planar sheet of material, for example, a metallic material, for example, Nitinol. In an alternative aspect of the invention, apparatus 1800 is heat treated prior to implantation, to take on a curved configuration, for example, similar to the curved configuration of apparatus 1700 shown in FIG. 29. The degree of curve may be selected based upon the needs of a particular patient. The heat treated curved apparatus 1800 may then be implanted into the pharyngeal region described elsewhere herein.

Figure 31:
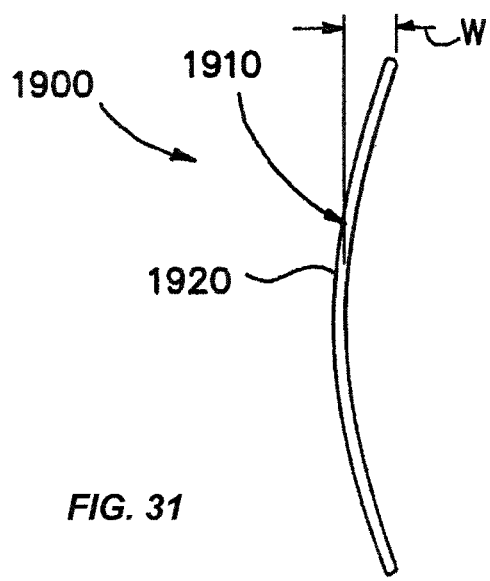
FIG. 31 shows a plan view of another embodiment of the invention comprising a substantially bow shaped element.

FIG. 31 shows a plan view of another apparatus 1900 for treating sleep apnea and/or snoring, in accordance with the present invention. The apparatus 1900 comprises an appliance 1910 including at least one substantially bow shaped element 1920. Apparatus 1900 is made of materials, e.g., metals, and includes only substantially smooth surfaces, preferably with no abrupt or sharp edges, to reduce or substantially eliminate fibrosis, as discussed previously with regard to apparatus 1600, 1700 and 1800.

The bow shaped element 1920 is structured to be substantially entirely submucosally implanted within the pharyngeal region, for example along a posterior wall and/or a lateral wall of the oropharyngeal region to provide an opening force to the region, such as described elsewhere herein. In one aspect of the invention, element 1920 has a thickness smaller than a length thereof, and is further sized and structured such that, when placed in the pharyngeal region, the element 1920 extends along the pharyngeal wall longitudinally a distance greater than the thickness of the element. For example, the element 1920 may be sized and structured to be placed somewhat angularly with respect to a longitudinal axis of the pharynx or pharyngeal region as distinguished from being sized and structured to be placed directly traverse or perpendicular to the longitudinal axis of the pharynx.

The at least one element 1920 may, in some embodiments of the invention, comprise a plurality of such elements 1920, meaning two or more such elements 1920, with each element having the same or different dimensions and structured and sized to be placed in a spaced apart, for example, laterally and/or longitudinally spaced apart, relationship within the pharyngeal region. Alternatively, the two or more bow shaped elements 1920 may be structured and sized to be placed in the pharyngeal region in a crosswise arrangement, for example, in an arrangement such that the elements 1920 overlap or cross one another, or in any other suitable arrangement effective to treat sleep apnea and/or snoring.

Depending upon where support is needed, and/or depending upon an amount or degree of support or reinforcement needed in a particular patient, and/or depending on one or more other factors, the element or elements 1920 may be disposed generally horizontal or perpendicular to the longitudinal axis of the pharynx or pharyngeal region or, alternatively, at any other suitable angle thereto.

Figure 31A:
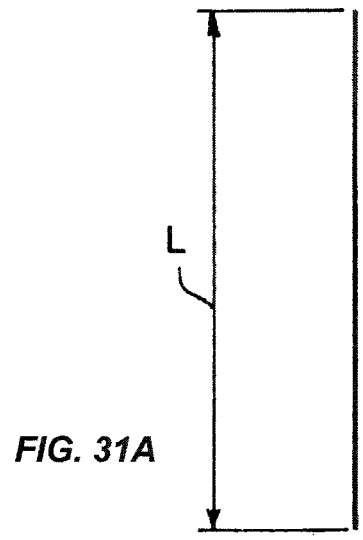
FIG. 31A shows a side view of the embodiment of the invention shown in FIG. 31.

Referring to both FIGS. 31 and 31A, element 1920 may substantially define an arc having a radius of curvature of about 2.481 inches (about 63 mm). Each end of the element 1920 may have a radius of curvature about 0.020 inch (about 0.50 mm). Element 1920 may have a length L, measured in a straight line between ends of the element 1920, of about 1.964 inches (about 50 mm) and an arched width W of about 0.196 inches (about 5.0 mm), as shown. The element 1920 may have a width, for example, a substantially uniform width along the arc of the element 1920, of about 0.039 inch (about 1.0 mm). The element 1920 may have a thickness of about 0.008 inch (about 0.20 mm).

Figure 32:
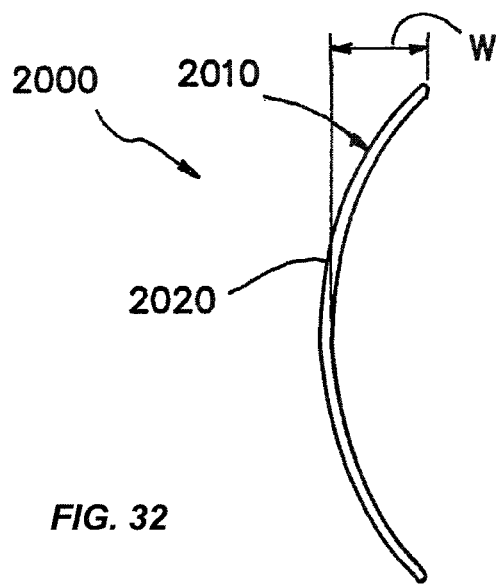
FIG. 32 shows a plan view of yet another embodiment of the invention similar to the embodiment shown in FIG. 31 but having a different radius of curvature.

FIG. 32 shows a plan view of another apparatus 2000 comprising an apparatus 2010 including an element 2020 that, like element 1920, is substantially arcuate or bow shaped. This embodiment of the invention is substantially identical to the embodiment, apparatus 1900, shown in FIG. 31 and FIG. 31A, with the exception of some of the dimensions thereof.

Figure 32A:
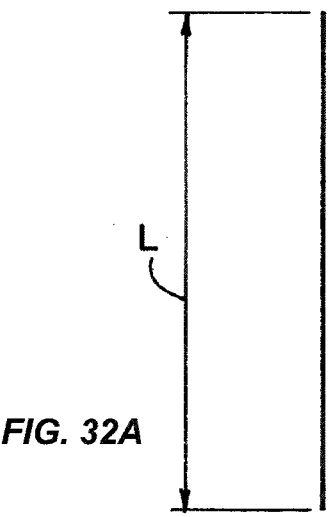
FIG. 32A shows a side view of the embodiment of the invention shown in FIG. 32.

Referring to both FIGS. 32 and 32A, element 2020 may substantially define an arc having a radius of curvature of about 1.392 inches (about 35 mm). Each end of the element 2020 may have a radius of curvature about R 0.020. Element 2020 may have a length L, measured in a straight line between ends of the element 2020, of about 1.964 inches (about 50 mm), an arched width W of about 0.394 inch (about 10 mm). The element 2020 may have a width, for example, a substantially uniform width along the arc of the element 2020, of about 0.039 inch (about 1.0 mm). The element 2020 may have a thickness of about 0.008 inch (about 0.20 mm).

It will be appreciated by those of skill in the art that not all possible variations of the apparatus for treating sleep apnea and/or snoring are shown, and that there are many other variations of the apparatus that are structured and shaped to provide specific support to different areas of the pharyngeal region, for example, the oropharyngeal region in order to treat sleep apnea and/or snoring, and based on the specific needs of a particular patient. Each of these variations is considered to be within the scope of the present invention.

In yet another broad aspect of the present invention, methods are provided for maintaining patency of a pharyngeal region, for example, the oropharyngeal region, in order to substantially reduce the occurrence of sleep apnea and/or snoring. These methods in accordance with the invention comprise, for example, steps of strengthening, reinforcing and/or stiffening tissues of the region which are subject to collapse during natural sleep. For example, this may be accomplished by any one or more of the following steps:

injecting an agent into the tissues which will cause partial necrosis of portions of the tissues in the region, thereby stiffening the region; injecting, into the tissues, a liquid or gel agent that solidifies within the region to provide a reinforcement against collapse of the region; mechanically or chemically irritating the tissues to cause a tissue reaction that firms the tissues of the region; and applying a wave energy to the tissues to cause a tissue reaction that firms the tissues of the region, for example, but not limited to ultrasonic energy, radiofrequency energy, thermal energy (either adding thermal energy to the tissues or chilling the tissue by removing thermal energy). Combinations of two or more of these steps may be advantageously employed.

A preferred method for maintaining patency of a pharyngeal region, in accordance with the present invention, generally comprises providing a member, for example elongated element 1401, element 1920, element 2020, in a substantially flat or precurved configuration. The member has a body portion and end portions spaced apart by the body portion. The member is implanted, at least partially submucosally, within the pharyngeal region, preferably the oropharyngeal region, such that the member is effective to provide a substantially constant force against at least a portion of each of the lateral walls of the region.

Preferably, the step of implanting comprises implanting the member into the pharyngeal region such that the member is substantially entirely submucosally implanted in the pharyngeal region.

For example, the member may be implanted into oropharyngeal tissues, preferably directly beneath the mucosal layer, by using a curved surgical needle to weave or otherwise introduce the member into and beneath the submucosal tissue.

In another embodiment of the invention, the method comprises the steps of providing an apparatus in the oropharyngeal region of the human or animal, for purposes other than surgery. The apparatus is effective in treating sleep apnea and/or snoring and/or in maintaining patency of the oropharyngeal region during natural sleep of the human or animal, without causing substantial interference with one or more natural functions of the epiglottis.

Each of the apparatus for treating sleep apnea and/or snoring described and shown elsewhere herein are suitable for use in the methods of the present invention. It is to be appreciated, however, that the apparatus used for performing the methods of the invention may take other forms as well. For example, it is contemplated herein that a conventional stent may be used in maintaining the airway in the pharyngeal region, for example, the oropharyngeal region in an open state, and such use is considered to be within the scope of the methods of the present invention. The apparatus used in the methods of present invention may be devices, for example but not limited to, a conventional stent, sized and structured for placement in another region of the human or animal other than the pharyngeal region, for example, the oropharyngeal region.

In another embodiment of the invention, a method for maintaining patency of a pharyngeal region of a patient comprises the steps of providing an apparatus in a first configuration, for example a rolled, coiled, or otherwise deformed configuration; inserting the apparatus into the oropharyngeal region, for example through the oral or nasal cavity of the patient while the apparatus is in a first configuration; and, thereafter, allowing the apparatus to reconfigure or expand to a deployed second configuration, for example a substantially cuff shaped, C-shaped, or other suitable deployed configuration, within the oropharyngeal region.

Any suitable deployment assembly useful for inserting the apparatus through the mouth or oral cavity, or nasal cavity of a patient and into the oropharyngeal region may be utilized in accordance with the methods of the present invention.

For example, a suitable deployment assembly includes an outer tube (about 10 mm diameter) and inner tube (about 8 mm diameter) disposed within the outer tube. A retaining clip may be used to fix the tubes in place with respect to each other. The appliance, for example in rolled form, is provided within the outer tube at a distal portion thereof. Graspers, having a manually manipulable proximal portion may be provided through the tubes for assisting in positioning or removal of the appliance.

During insertion through the mouth or oral cavity of the patient, the deployment assembly is advanced past the tongue of the patient until the inner diameter of the outer tube and the rolled appliance passes into the oropharyngeal region. The retaining clip is then removed from the inner tube. The graspers may be used to facilitate repositioning of the appliance as necessary or desirable. The appliance is deployed by retraction of the outer tube. (The assembly/graspers may be used to later remove the appliance if desired).

In a more specific, related embodiment of the invention, the following method is provided. This method generally comprises the steps of providing a flat or pre-curved member (for example, appliance 110, 210, 310, 410, 510, 610, 710, 810 910, 1010, 1110 or 1120 shown in the drawings), pulling end portions of the flat or pre-curved member together to form a folded member and holding or temporarily securing the end portions together by means of a grasper, clamp, hemostat, suture (for example, a bioresorbable suture), and/or suitable means for temporarily holding the end portions together in contact with one another. The method further comprises the steps of placing the member in the folded or pinched configuration, into the oropharyngeal region, for example by way of the oral or nasal cavity of the patient, and releasing the end portions, thereby allowing the member to expand radially within the oropharyngeal region to provide a substantially constant radial force against the lateral walls of the oropharyngeal region and/or the base of the tongue.

The method may further comprise the step of repositioning the member while the member is located within the oropharyngeal region and/or the step of removing the member therefrom. This may be accomplished by folding the member into a rolled or pinched configuration and withdrawing the member from the body region.

Example 1

A 40-year-old, 5-foot, 11 in., 350 lb male is referred by his primary care physician for evaluation of sleep disturbance. He experiences snoring with apneic pauses, and severe daytime hypersomnolence with narcolepsy, and has so for many years. His occupation as a truck driver has been jeopardized by this behavior. Several years prior, he underwent uvulopalatoplasty (UPPP) and tonsillectomy, without any significant relief of his symptoms. The patient claims that the use of CPAP was attempted, but was unsuccessful.

A polysomnography is performed indicating a Respiratory Disturbance Index (RDI) of 113.4 with severe desaturations, bradycardia, and complete absence of stage 3, stage 4, and REM sleep. CPAP therapy was titrated to 18, cm of water, but the patient's RDI remained elevated at 60 with ongoing, severe desaturations.

Appliance 1400 having a length of about 70 mm and a width of about 1.0 mm and a thickness of about 0.0075 inches (about 0.2 mm), is selected by the physician for submucosal implantation.

Under general anesthesia, and using direct laryngoscopy techniques, the appliance is introduced into the submucosal tissues beginning in the right lateral pharyngeal region, particularly the right lateral oropharyngeal region. The appliance is introduced submucosally using a curved surgical needle which is used to carefully pull the appliance into the tissues in a manner that causes the appliance to be substantially concealed within the tissues, with little or no exposure of any portion of the appliance postsurgically.

The appliance is guided medially, and inferiorly, traveling around the posterior oropharyngeal region and ultimately into the submucosal tissues of the tongue base. The tongue base is then traversed and the appliance is brought back along the right lateral oropharyngeal wall. The appliance thus makes at least one complete rotation around the pharynx. Careful microscopic examination of the pharyngeal tissues reveals no areas of appliance exposure. Extubation proceeds without difficulty, and the patient is closely observed overnight.

During the first week of recovery, the patient reports having some desire to cough out the device, throat pain, dysphagia, and hoarseness.

However, by the end of the first week, these symptoms are reported as minimal. Further, the patient indicates a significant reduction in effort, wheezing, and noise during daytime breathing. A CT Scan is performed to confirm adequate device placement and integrity. A modified barium swallow study is obtained at the end of the second week. This study indicates that the appliance is intact, allowing normal swallowing in the pharyngeal region and appears to be providing circumferential support to the oropharyngeal region.

Polysomnography is repeated at two weeks, showing significant improvements in oxygen saturations and RDI.

Example 2

A 50 year old, 5 foot 4, 180 pound, female patient complains of severe hypersomnolence. It is additionally noted that the patient's spouse has long complained of the patient's substantial nightly snoring and has witnessed pauses in the patient's breathing followed by gasping for air when she sleeps (believed to be apneic pauses).

Following clinical tests and evaluation of patient history, the patient is diagnosed with severe sleep apnea.

An appliance 1400 is selected for implantation in the patient. In this example, the appliance 1400 is made of Nitinol and has a length of about 40 mm, a width of 1.25 mm and a thickness of about 0.5 mm.

Under general anesthesia, and using direct laryngoscopy techniques, the appliance is introduced into the submucosal tissues beginning in the right lateral oropharyngeal region. The appliance is then guided medially, and inferiorly, traveling around the posterior oropharyngeal region and ultimately into the submucosal tissues of the left lateral oropharynx. The appliance does not traverse the tongue. The appliance thus makes about a 180 degree rotation around the oropharynx.

Careful microscopic examination of the oropharyngeal tissues reveals no areas of appliance exposure. Extubation proceeds without difficulty, and the patient is closely observed overnight.

Within two weeks, the patient reports feeling more energy during the daytime and alertness upon awakening. Her husband remarks that the patient's snoring has substantially decreased and she does not seem to be experiencing apneic pauses during the night.

While this invention has been described with respect to various specific examples and embodiments, it is to be understood that the invention is not limited thereto and that it can be variously practiced within the scope of the following claims.

We claim:

1. A method for treating obstructive sleep apnea of a patient, comprising:
   a) providing an arcuate support structure that is adapted for implant in an airway of the patient comprising a tongue movement resisting member;
   b) implanting the arcuate support member into the patient's pharynx; and
   c) preventing the complete closure of the airway by stopping the patient's tongue from complete collapse and blockage of substantially all airflow,
   wherein the arcuate support structure comprises first and second end portions, each of the first and second end portions comprising a tongue movement resisting member, and
   wherein the arcuate support structure comprises one or more protrusions located between the first and second end portions, and wherein the arcuate support structure is implanted into the pharynx such that the one or more protrusions are disposed on a posterior wall of the pharynx.

2. The method of claim 1, wherein the first and second end portions extend around opposite lateral walls of the pharynx to support the tongue sufficiently to stop the tongue from complete collapse and blockage of substantially all airflow.

3. The method of claim 1, wherein the arcuate support structure extends around the pharynx such that the first and second end portions traverse a base of the tongue to stop the tongue from complete collapse and blockage of substantially all airflow.

4. The method of claim 1, wherein the support structure is generally planar in a resting state, and wherein providing an arcuate support structure comprises rolling or folding the support structure into an arcuate configuration before inserting the support structure into the pharynx.

5. The method of claim 1, wherein the support structure is "C" shaped in a resting state, and wherein the providing an arcuate support structure step comprises rolling or folding the arcuate support structure before inserting the support structure into the pharynx.

6. A method for treating obstructive sleep apnea of a patient, comprising:
   a) providing an arcuate support structure defining a lumen comprising one or more flexible members; and
   b) implanting the arcuate support structure into the patient's pharynx,
   c) the one or more flexible members flex allowing adjacent tissue
   or organs to encroach on the lumen of the arcuate support structure while preventing complete closure of the patient's airway while allowing the patient's tongue to contact a wall of the pharynx, wherein the one or more flexible members comprise first and second end portions of the arcuate support structure, and wherein the arcuate support structure comprises one or more protrusions located between the first and second end portions, and wherein the arcuate support structure is implanted into the pharynx such that the one or more protrusions are disposed on a posterior wall of the pharynx.

7. The method of claim 6, wherein the first and second end portions extend around opposite lateral walls of the pharynx to support the tongue sufficiently to prevent the complete closure of the airway.

8. The method of claim 6, wherein the arcuate support structure extends around the pharynx such that the first and second end portions traverse a base of the tongue to prevent complete closure of the airway.

9. The method of claim 6, wherein the one or more flexible members are sufficiently flexible such that, upon contraction of the pharynx during swallowing, the one or more flexible members are temporarily forced toward one another.

* * * * *